United States Patent [19]

Nohira et al.

[11] Patent Number: 5,194,177

[45] Date of Patent: Mar. 16, 1993

[54] OPTICALLY ACTIVE COMPOUND, LIQUID CRYSTAL COMPOSITION, LIQUID CRYSTAL DEVICE, DISPLAY APPARATUS AND DISPLAY METHOD

[75] Inventors: Hiroyuki Nohira, Urawa; Takao Takiguchi, Tokyo; Takashi Iwaki, Machida; Takeshi Togano, Yokohama; Yoko Yamada; Shinichi Nakamura, both of Atsugi, all of Japan

[73] Assignee: Canon Kabushiki Kaisha, Tokyo, Japan

[21] Appl. No.: 822,675

[22] Filed: Jan. 21, 1992

[30] Foreign Application Priority Data

Jan. 30, 1991 [JP] Japan .................. 3-009834

[51] Int. Cl.$^5$ .................. C09K 19/34; C07D 277/62; G02F 1/13
[52] U.S. Cl. .................. 252/299.61; 252/299.62; 252/299.7; 359/104; 359/105; 548/146; 548/153; 548/179; 548/181
[58] Field of Search .................. 252/299.01, 299.61, 252/299.62, 299.63, 299.7; 359/76, 79, 104, 105; 548/146, 153, 179, 181

[56] References Cited

U.S. PATENT DOCUMENTS

| | | | |
|---|---|---|---|
| 4,367,924 | 1/1983 | Clark et al. | 359/56 |
| 4,867,903 | 9/1989 | Nohira et al. | 252/299.61 |
| 4,873,018 | 10/1989 | Nohira et al. | 252/299.01 |
| 4,918,213 | 4/1990 | Nohira et al. | 558/271 |
| 5,034,151 | 7/1991 | Shinjo et al. | 252/299.61 |
| 5,073,306 | 12/1991 | Nohira et al. | 252/299.61 |
| 5,075,030 | 12/1991 | Togano et al. | 252/299.61 |
| 5,075,031 | 12/1991 | Nohira et al. | 252/299.61 |
| 5,076,961 | 12/1991 | Nakamura et al. | 252/299.61 |
| 5,091,109 | 2/1992 | Takiguchi et al. | 252/299.61 |
| 5,098,600 | 3/1992 | Nakamura et al. | 252/299.61 |

FOREIGN PATENT DOCUMENTS 393613 10/1990 European Pat. Off. .
107216 8/1981 Japan .
067237 3/1990 Japan .

OTHER PUBLICATIONS

Comptes Rendus, vol. 282, No. 14 (1976) Series C-639:41.
Journal of Applied Physics, vol. 45, No. 11 (1974) 4718:23.
Physical Review Letters, vol. 20, No. 19 (1968) 1024:1028.
Applied Physics Letters, vol. 18, No. 4 (1971) 127:128.

*Primary Examiner*—Robert L. Stoll
*Assistant Examiner*—Shean C. Wu
*Attorney, Agent, or Firm*—Fitzpatrick, Cella, Harper & Scinto

[57] ABSTRACT

An optically active compound represented by the following formula (I):

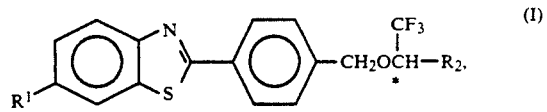

wherein $R_1$ denotes a linear or branched alkyl group having 1-18 carbon atoms optionally including one or non-neighboring two or more methylene groups which can be replaced with —X— or

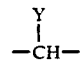

with the proviso that X denotes O or S and Y denotes halogen; $R_2$ denotes a linear alkyl group having 4-8 carbon atoms: and C* denotes an optically active asymmetric carbon atom. The mesomorphic compound is effective for providing a ferroelectric liquid crystal composition showing improved response characteristics and also effective for suppressing occurrence of reverse domain.

28 Claims, 4 Drawing Sheets

OPTICALLY ACTIVE COMPOUND, LIQUID CRYSTAL COMPOSITION, LIQUID CRYSTAL DEVICE, DISPLAY APPARATUS AND DISPLAY METHOD

FIELD OF THE INVENTION AND RELATED ART

The present invention relates to a novel optically active compound, a liquid crystal composition a liquid crystal device, a display apparatus and a display method, and more particularly to a novel optically active compound having a trifluoromethyl group incorporated into an optically active site, a liquid crystal composition containing the optically active compound, a liquid crystal device using the liquid crystal composition, a display apparatus using the device, and a display method using the composition and device.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

However, when the above-mentioned TN liquid crystal is used in a device having a matrix electrode structure with high packing density of picture elements and subjected to a multiplex driving scheme, there occurs crosstalk and thus the number of the picture elements is restricted. In addition, a use for the above device as a display device is also restricted due to slow response to an electric field and a poor view angle characteristic.

There has been known a display device wherein a switching device comprising a thin film transistor (TFT) is connected to each picture element to effect switching. However, such a display device has problems that not only a step of forming a TFT on a substrate is very complicated but also it is difficult to prepare a display device with a large picture area.

To overcome drawbacks with such prior art liquid crystal devices, the use of liquid crystal devices having bistability has been proposed by Clark and Lagerwall (e.g. Japanese Laid-Open Patent Appln. No. 56-107216; U.S. Pat. No. 4,367,924, etc.). In this instance, as the liquid crystals having bistability, ferroelectric liquid crystals having chiral smectic C-phase (SmC*) or H-phase (SmH*) are generally used.

Such a ferroelectric liquid crystal (hereinafter, sometimes abbreviated as "FLC") has spontaneous polarization to provide a high-speed responsiveness and bistable states of first and second stable states each having a memory characteristic of retaining each state in the absence of an electric field and is also excellent in a view angle characteristic, so that the liquid crystal is suitable for providing a display device with a large image area and high packing density of picture elements.

The ferroelectric liquid crystal has an asymmetric carbon atom and used in a display device utilizing its chiral smectic C phase. In addition to the above use, the ferroelectric liquid crystal can also be used as optical devices characterized by having optical activities as will be exemplified as follows:

1) Those utilizing a cholesteric-nematic phase transition in ia liquid crystal state (J. J. Wysoki, A. Adams and W. Haas: Phys. Rev. Lett., 20, 1024 (1968); and 2) Those utilizing a guest-host effect of the White-Taylor type in a liquid crystal state (D. L. White and G. N. Taylor: J. Appl. Phys., 45, 4718 (1974)).

These optical devices are important as display devices and modulation devices, while the explanation of the individual systems is left to the respective references and omitted.

In such optical devices utilizing an electric field-responsive optical effect in a liquid crystal state, it has been preferably practiced to introduce a polar group so as to improve the responsiveness.

It has been especially known for a ferroelectric liquid crystal that the response speed is proportional to its spontaneous polarization, so that it is desired to increase the spontaneous polarization for achieving a high speed driving. From such a viewpoint, P. Keller et al have shown that it is possible to realize a higher response speed through increase in spontaneous polarization by introducing a cholrine atom so as to be bonded to an asymmetric carbon atom (C.R. Acad. Sc. Paris, 282 C, 639 (1976)). However, the chlorine atom bonded to the asymmetric carbon atom is chemically unstable and has a large atomic radius so that the stability of the liquid crystal phase is lowered. Accordingly, an improvement is still desired.

On the other hand, many of functional materials constituting the optical devices characterized by optical activity are synthesized through an intermediate which per se is optically active.

Heretofore, as optically active intermediates for synthesizing such functional materials necessary for such optical devices, those compounds are known such as 2-methylbutanol, sec-octyl alcohol, sec-butyl alcohol, p-(2-methylbutyl)benzoic acid chloride, sec-phenethyl alcohol, amino acid derivatives, camphor derivatives and cholesterol derivatives.

However, it has not been practiced to introduce a polar group into the above optically active intermediates in many cases, thus failing to effectively use a method of introducing a polar group so as to be bonded to an asymmetric carbon atom.

SUMMARY OF THE INVENTION

An object of the present invention is, in view of the above problems, to provide an optically active compound having an improved polarity by directly introducing a trifluoromethyl group so as to be bonded to an asymmetric carbon atom showing optical activity.

Another object of the present invention is to provide a liquid crystal composition containing at least one optically active compound described above and having a large spontaneous polarization and improved electric field-responsiveness, a liquid crystal device using the composition, a display apparatus using the device and a display method utilizing the composition or the device.

According to the present invention, there is provided an optically active compound represented by the following formula (I):

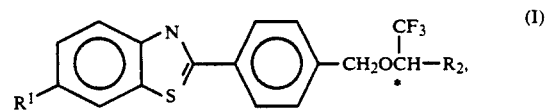

wherein $R_1$ denotes a linear or branched alkyl group having 1-18 carbon atoms optionally including one or non-neighboring two or more methylene groups which can be replaced with —X— or

the proviso that X denotes O or S and Y denotes halogen; $R_2$ denotes a linear alkyl group having 4-8 carbon atoms; and C* denotes an optically active asymmetric carbon atoms.

According to the present invention, there is further provided a liquid crystal composition containing at least one species of the compound described above.

The present invention provides a liquid crystal device comprising a pair of electrode plates and the liquid crystal composition described above disposed between the electrode plates.

The present invention further provides a display apparatus comprising the liquid crystal device, and voltage application means for driving the liquid crystal device.

The present invention still further provides a display method using the liquid crystal composition or the liquid crystal device described above and switching the alignment direction of liquid crystal molecules by applying voltages to the liquid crystal composition to effect display.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
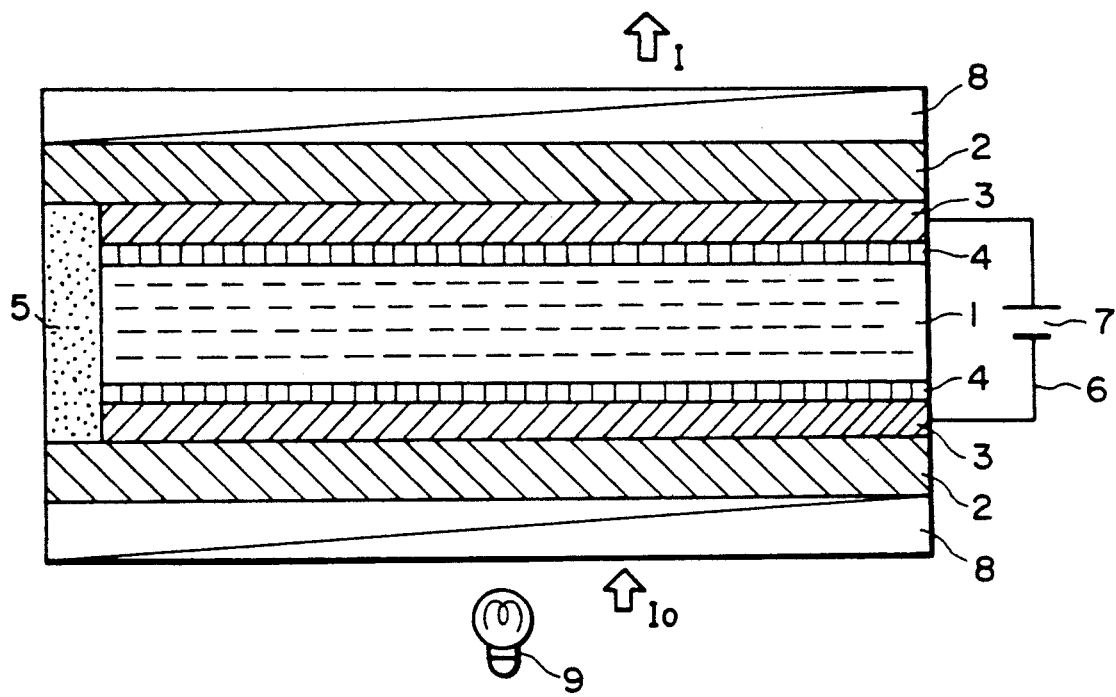
FIG. 1 is a schematic sectional view of a liquid crystal display device using a liquid crystal composition assuming a chiral smectic phase.

In the formula (I as described above, preferred examples of $R_1$ may include the following groups (i) to (iv):

(i) —G—$C_aH_{2a+1}$—n wherein G denotes a single bond, —O— or —S—; and a is an integer of 1-18, particularly 3-14;

(ii)

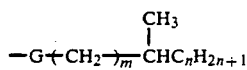

wherein G denotes a single bond, —O— or —S—; m is an integer of 0-7 and n is an integer of 1-9 (optically active or inactive);

(iii)

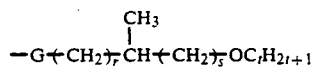

wherein G denotes a single bond, —O— or —S—;- r is an integer of 0-7; s is 0 or 1 and t is an integer of 1-14 (optically active or inactive); and (v)

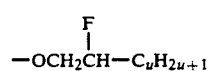

wherein u is an integer of 1-16 (optically active or inactive).

Preferred examples of $R_2$ may include a linear alkyl group having 4-6 carbon atoms.

Further, the compounds of the formula (I) may preferably be derived from an optically active 1,1,1-trifluoro-2-alkanol represented by the following formula (II):

wherein $R_3$ denotes a linear alkyl group having 4-8 carbon atoms and C* denotes an asymmetric carbon atom. The above compound of the formula (II) has been disclosed in Japanese Patent Application No. 218536/1988 by our research group.

The compounds represented by the formula (I) may generally be synthesized through the following reaction schemes A and B.

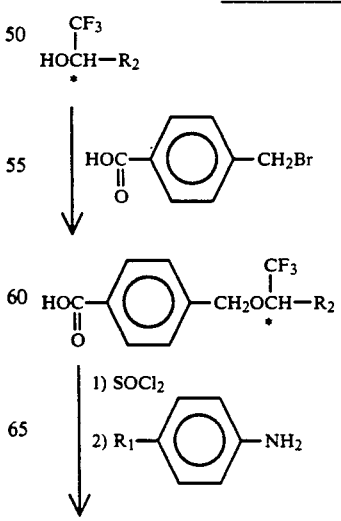

Reaction Scheme A

-continued
Reaction Scheme A
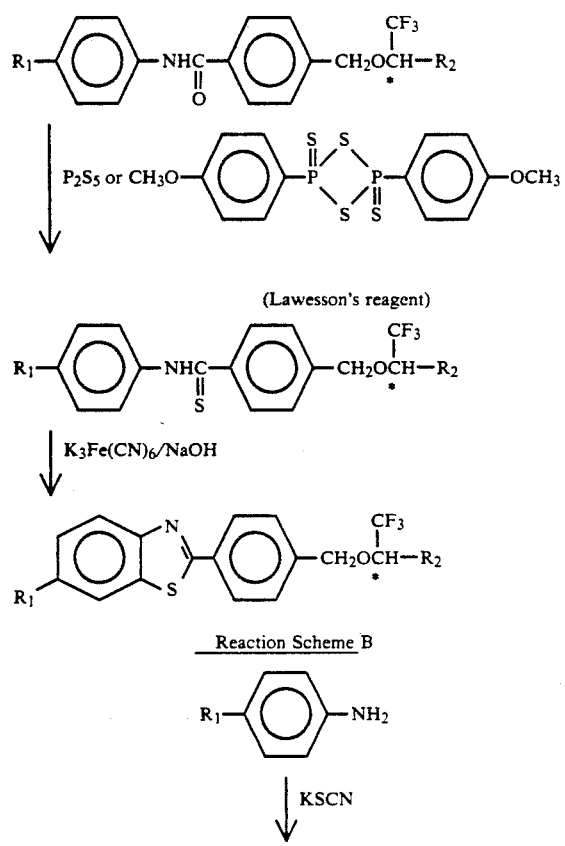
Reaction Scheme B
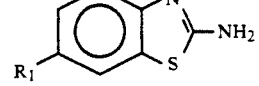
-continued
Reaction Scheme A
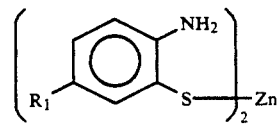
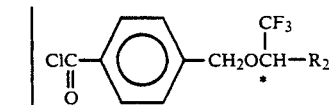
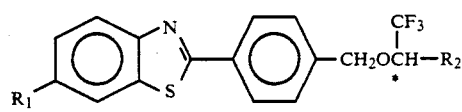
In the above, $R_1$ and $R_2$ denote the same as described hereinabove.
Specific examples of the compounds represented by the formula (I) may include those shown in the following structural formulas.
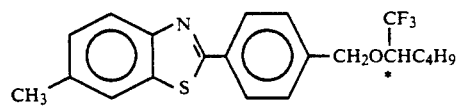 (1)
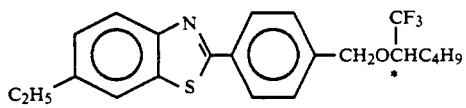 (2)
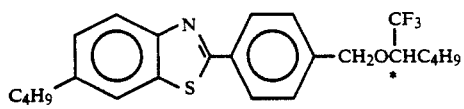 (3)
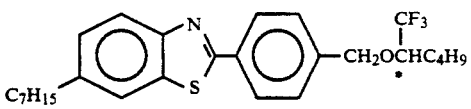 (4)
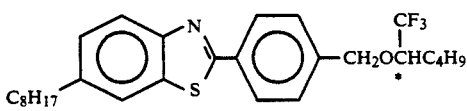 (5)
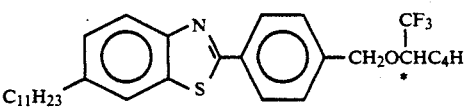 (6)
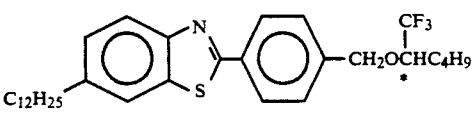 (7)
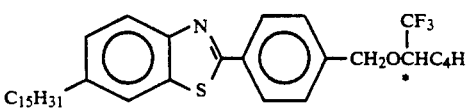 (8)
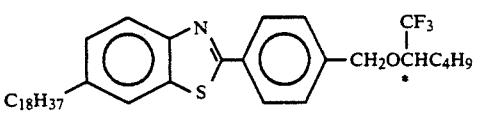 (9)
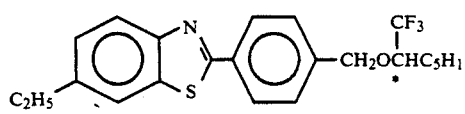 (10)

-continued
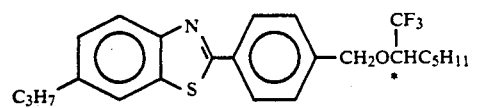 (11)
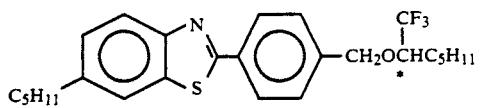 (12)
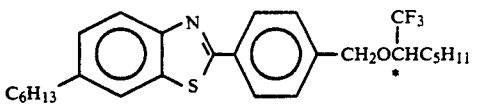 (13)
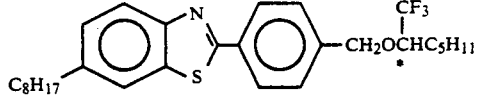 (14)
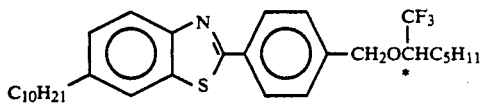 (15)
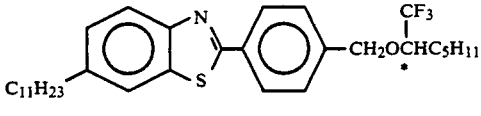 (16)
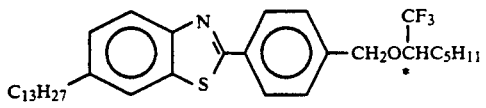 (17)
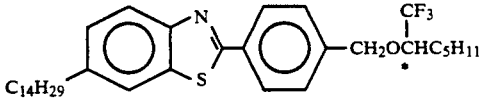 (18)
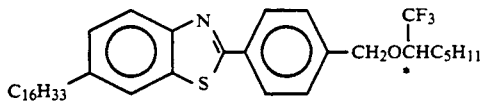 (19)
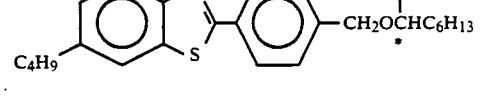 (20)
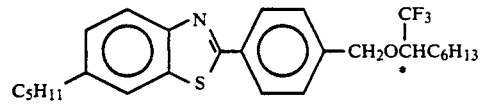 (21)
 (22)
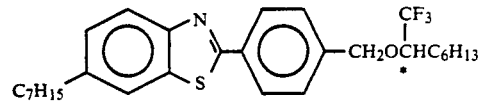 (23)
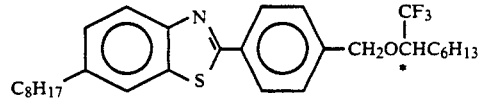 (24)
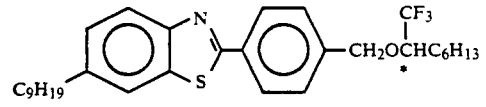 (25)
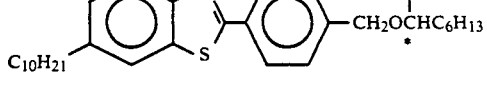 (26)
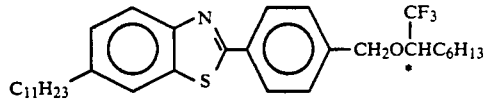 (27)
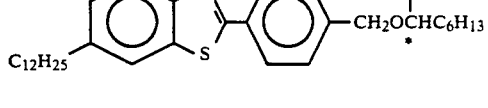 (28)
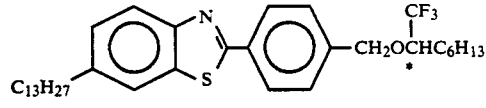 (29)
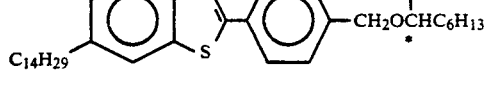 (30)
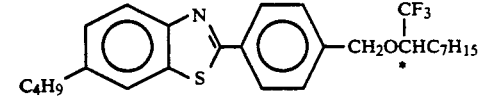 (31)
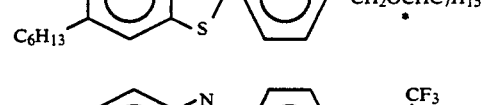 (32)
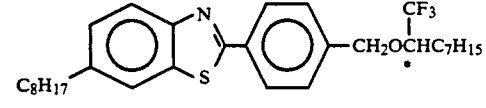 (33)
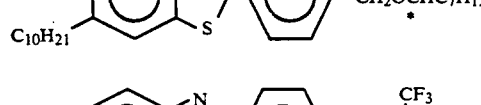 (34)
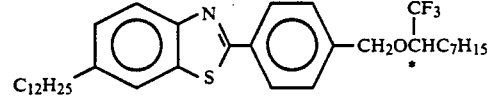 (35)
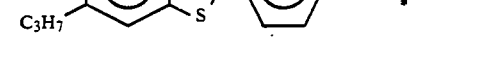 (36)

-continued
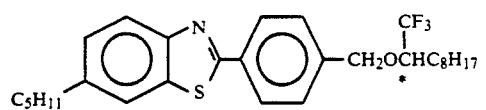 (37)
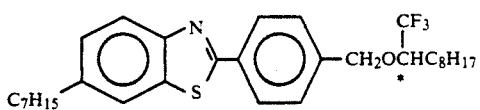 (38)
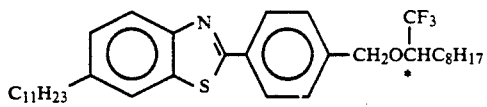 (39)
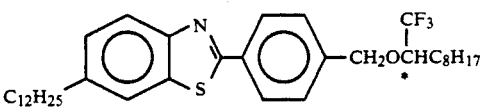 (40)
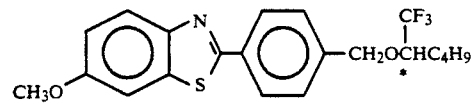 (41)
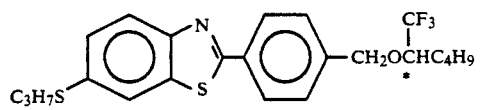 (42)
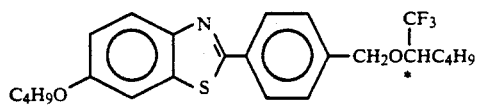 (43)
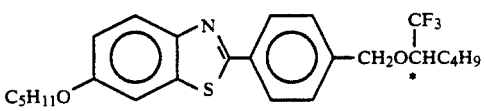 (44)
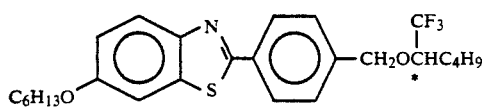 (45)
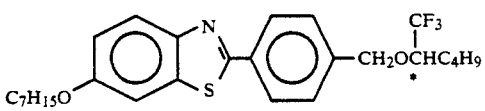 (46)
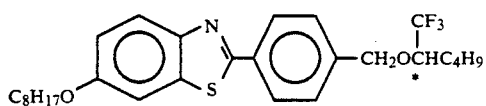 (47)
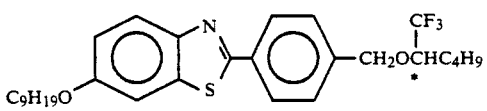 (48)
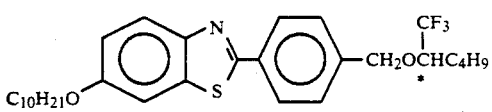 (49)
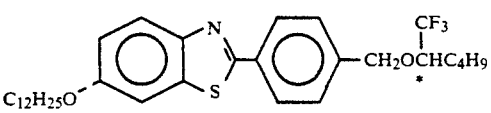 (50)
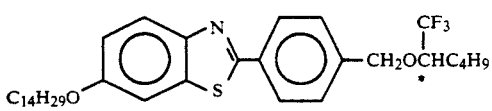 (51)
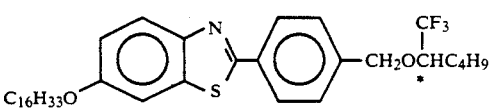 (52)
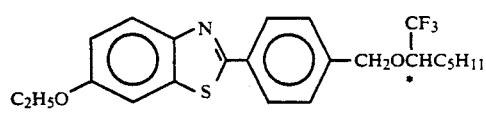 (53)
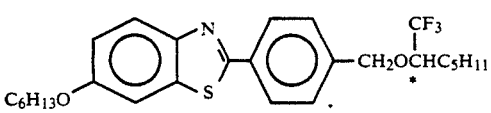 (54)
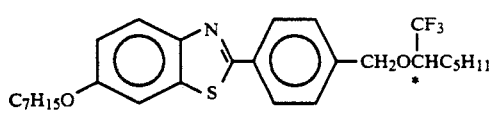 (55)
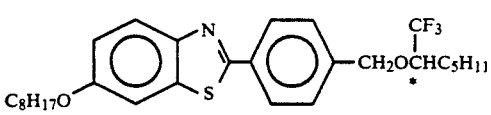 (56)
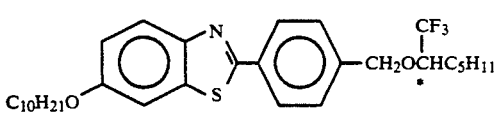 (57)
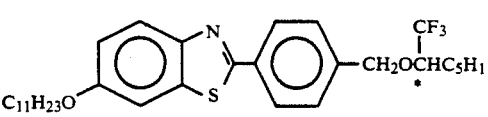 (58)
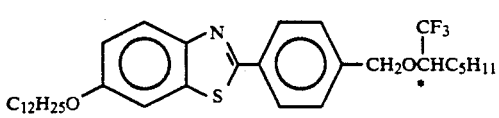 (59)
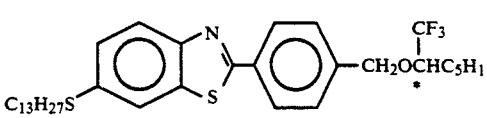 (60)
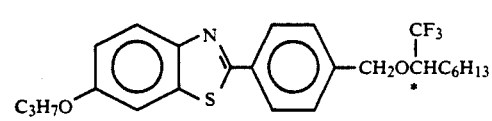 (61)
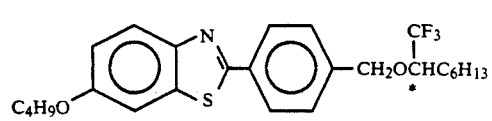 (62)

-continued
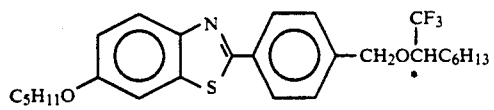
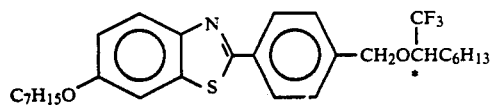
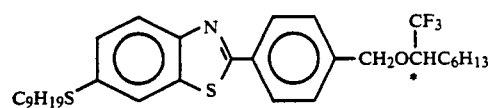
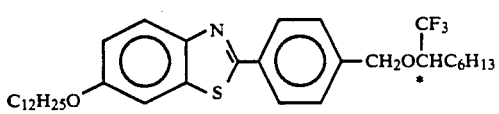
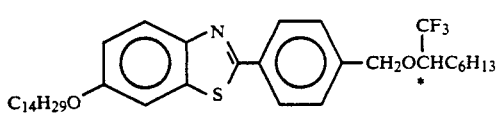
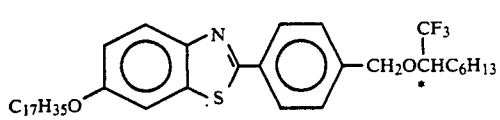
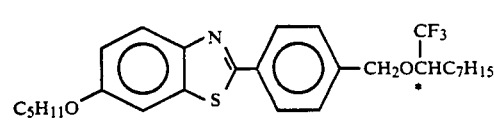
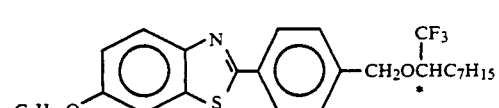
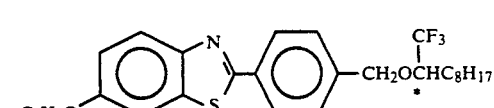
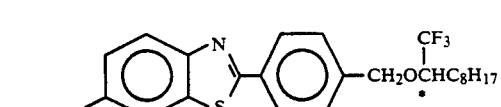
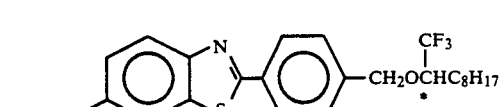
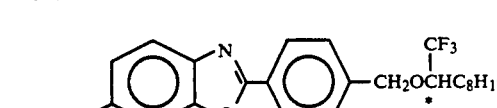
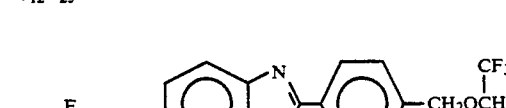
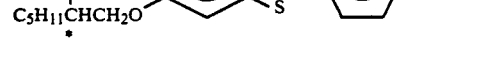

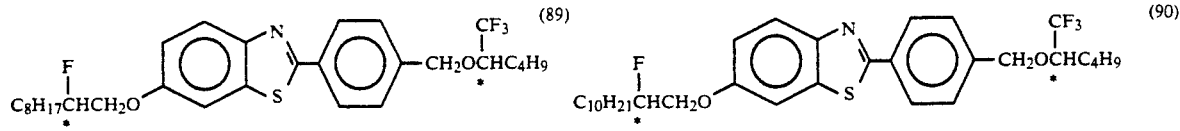
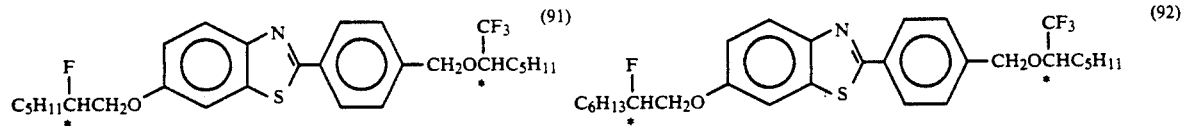
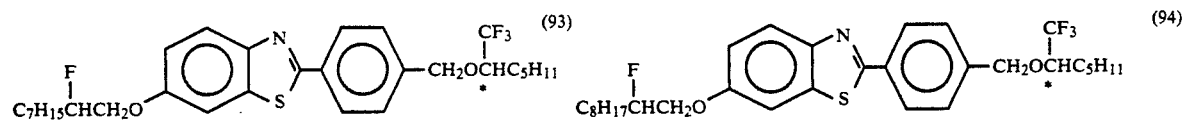
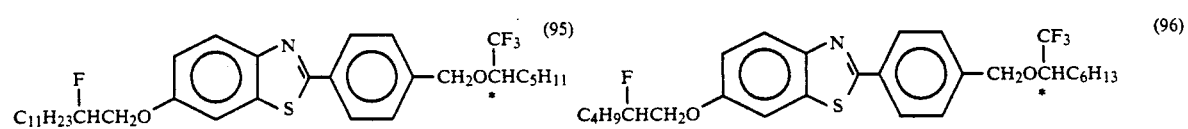
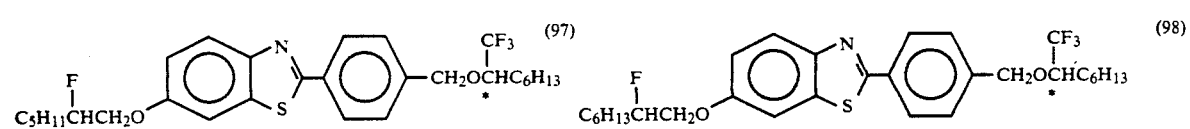
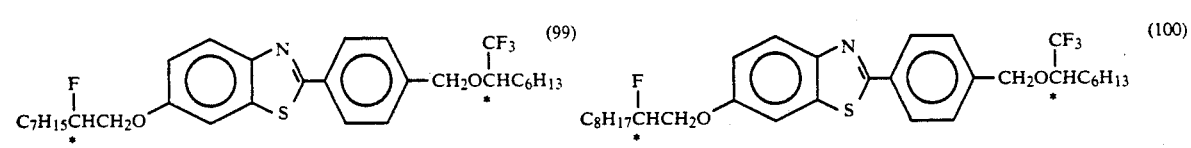
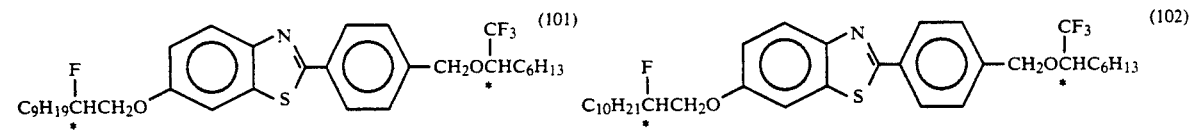
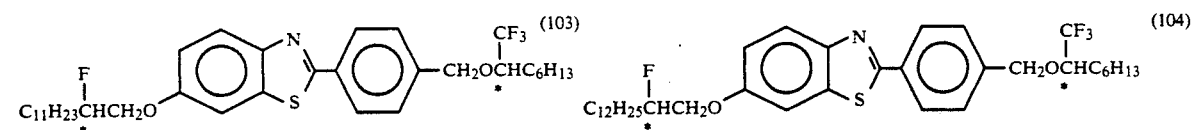
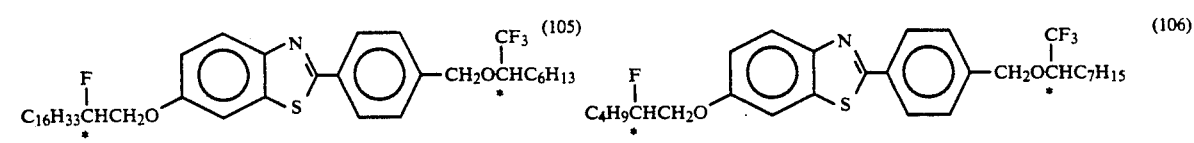
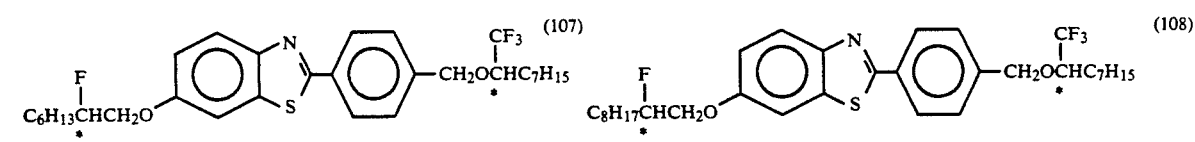
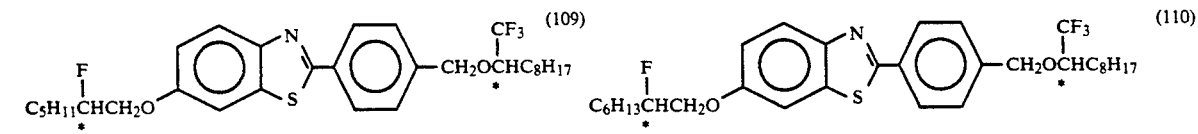

-continued

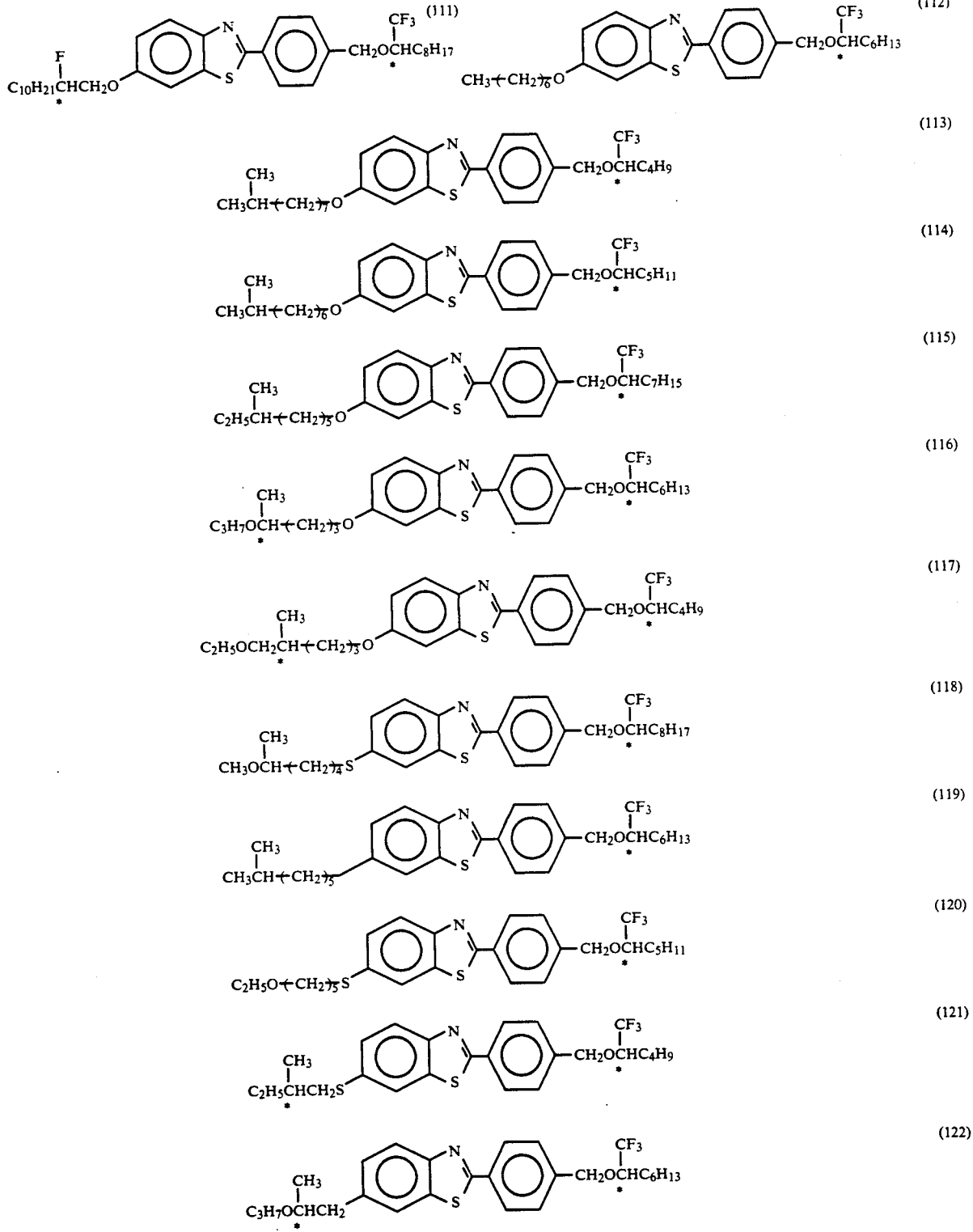

The liquid crystal composition according to the present invention may be obtained by mixing at least one species of the compound represented by the formula (I) and another mesomorphic compound in appropriate proportions.

In the composition, the compound of the formula (I) may show a mesomorphic phase alone or in combination with another mesomorphic compound. The liquid crystal composition according to the present invention may preferably be formulated as a liquid crystal composition capable of utilizing ferroelectricity, particularly a liquid crystal composition showing a chiral smectic phase.

Specific examples of another mesomorphic compound as described above may include those denoted by the following formulas (III) to (XII).

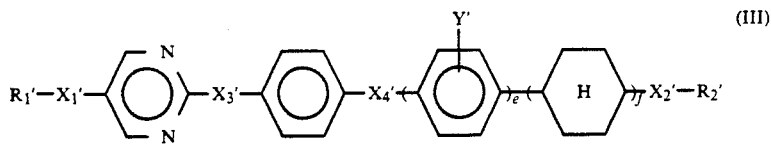
(III)

wherein e denotes 0 or 1 and f denotes 0 or 1 with proviso that e+f=0 or 1; Y' denotes H, halogen, CH$_3$ or CF$_3$; X$_1$' and X$_2$' respectively denote a single bond,

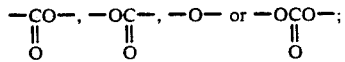

and X$_3$' and X$_4$' respectively denote a single bond,

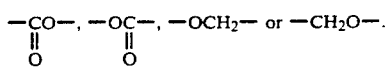

In the formula (III), preferred compounds thereof may include those represented by the following formulas (IIIa) to (IIId):

wherein g and h respectively denote 0 or 1 with proviso that g+h=1; i denotes 0 or 1; X$_1$' and X$_2$' respectively denote a single bond,

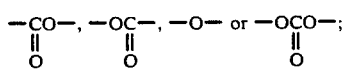

and X$_3$', X$_4$' and X$_5$' respectively denote a single bond,

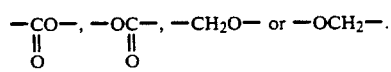

In the formula (IV), preferred compounds thereof may include those represented by the following formulas (IVa) to (IVc):

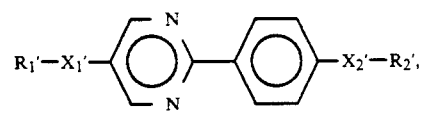
(IIIa)

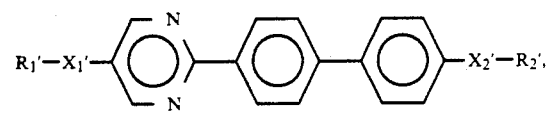
(IIIb)

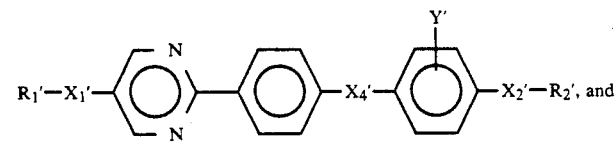
(IIIc)

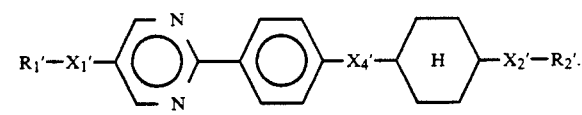
(IIId)

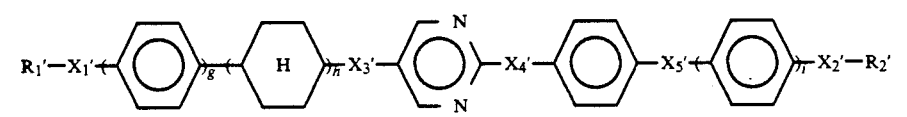
(IV)

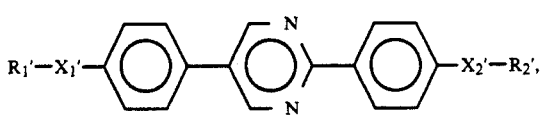
(IVa)

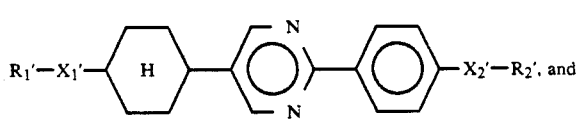
(IVb)

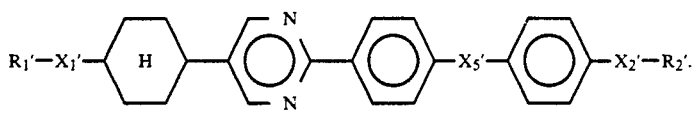

(IVc)

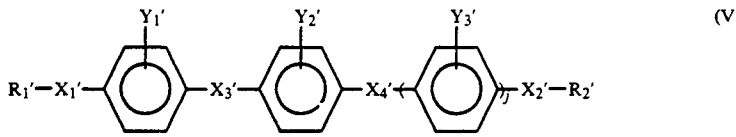

(V)

wherein j denotes 0 or 1; $Y_1'$, $Y_2'$ and $Y_3'$ respectively denote H, halogen, $CH_3$ or $CF_3$; $X_1'$ and $X_2'$ respectively denote a single bond,

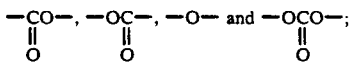

$-CO-$, $-OC-$, $-O-$ and $-OCO-$;

and $X_3'$ and $X_4'$ respectively denote a single bond,

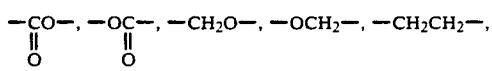

$-CO-$, $-OC-$, $-CH_2O-$, $-OCH_2-$, $-CH_2CH_2-$,

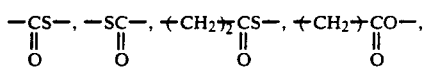

$-CS-$, $-SC-$, $+CH_2\!\!\!\frac{}{n}CS-$, $+CH_2\!\!\frac{}{}CO-$,

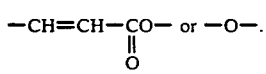

$-CH=CH-CO-$ or $-O-$.

In the formula (V), preferred compounds thereof may include those represented by the following formulas (Va) and (Vb):

In the formula (VI), preferred compounds thereof may include those represented by the following formulas (VIa) to (VIf):

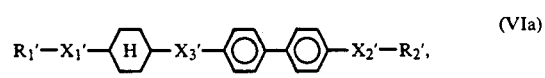
(VIa)

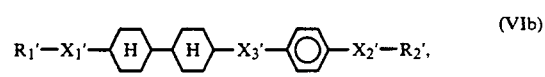
(VIb)

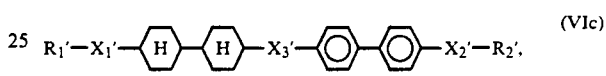
(VIc)

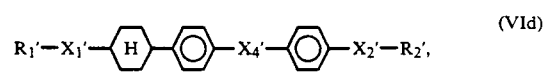
(VId)

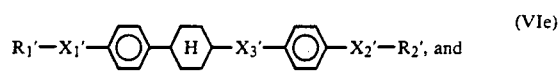
(VIe)

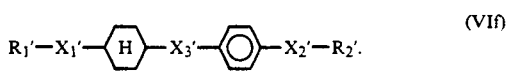
(VIf)

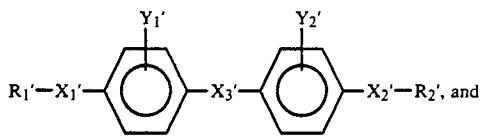
(Va)

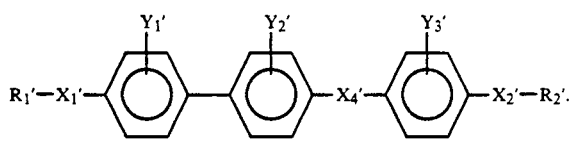
(Vb)

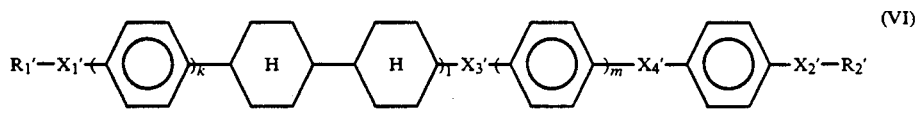
(VI)

wherein k, l and m respectively denote 0 or 1 with proviso that $k+l+m=0$, 1 or 2; $X_1'$ and $X_2'$ respectively denote a single bond,

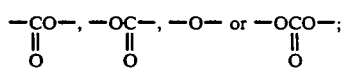

$-CO-$, $-OC-$, $-O-$ or $-OCO-$;

and $X_3'$ and $X_4'$ respectively denote a single bond,

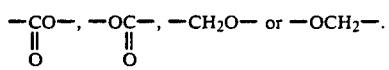

$-CO-$, $-OC-$, $-CH_2O-$ or $-OCH_2-$.

Herein, $R_1'$ and $R_2'$ respectively denote a linear or branched alkyl group having 1-18 carbon atoms capable of including one or non-neighboring two or more methylene groups which can be replaced with —CH halogen- and capable of further including one or two or more non-neighboring methylene groups other than those directly connected to $X_1'$ or $X_2'$ which can be replaced with at least one species of

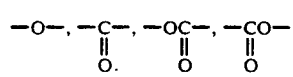

-continued

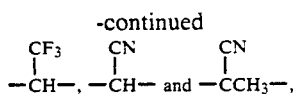

with proviso that $R_1'$ and $R_2'$ respectively do not connect to a ring structure by a single bond when $R_1'$ and $R_2'$ respectively denote a halogenated alkyl group containing one methylene group replaced with —CH halogen- or —CH(CF₃)—.

Further, preferred examples of $R_1'$ and $R_2'$ may respectively include those represented by the following groups (i) to (ix):

i) a linear alkyl group having 1-15 carbon atoms;

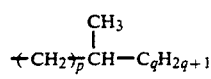

wherein p denotes an integer of 0-5 and q denotes an integer of 2-11 (optically active or inactive);

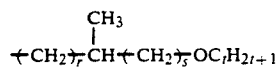

wherein r denotes an integer of 0-6, s denotes 0 or 1, and t denotes an integer of 1-14 (optically active or inactive);

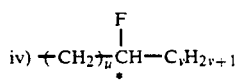

wherein u denotes 0 or 1 and v denotes an integer of 1-16;

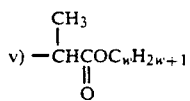

wherein w denotes an integer of 1-15 (optically active or inactive);

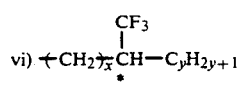

wherein x denotes an integer of 0-2 and y denotes an integer of 1-15.

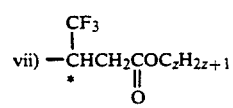

wherein z denotes an integer of 1-15.

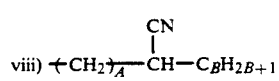

wherein A denotes an integer of 0-2 and B denotes an integer of 1-15 (optically active or inactive); and

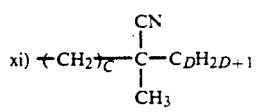

wherein C denotes an integer of 0-2 and D denotes an integer of 1-15 (optically active or inactive).

In the above-mentioned formula (III), more preferred compounds thereof may include those represented by the formulas (IIIaa) to (IIIdc):

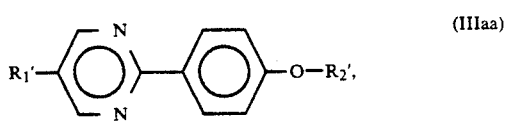

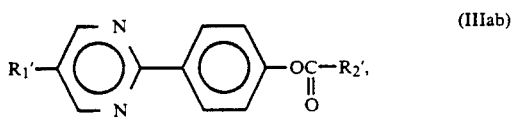

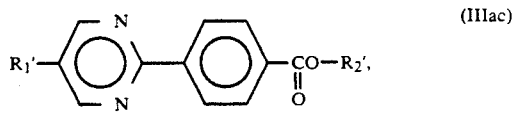

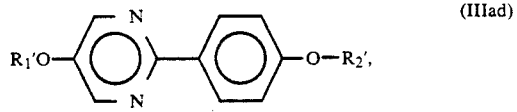

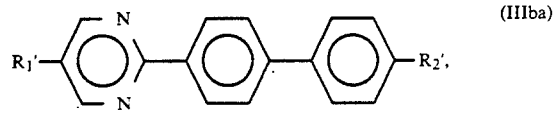

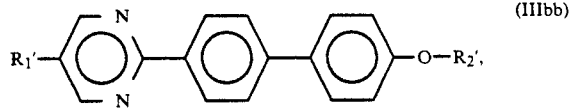

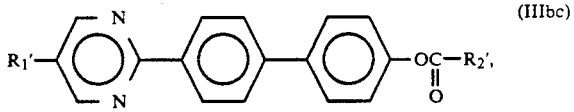

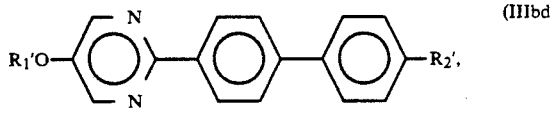

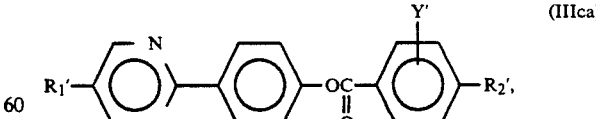

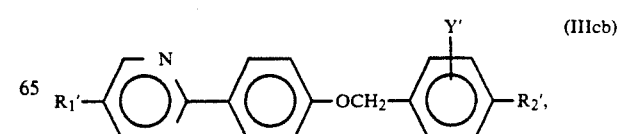

-continued
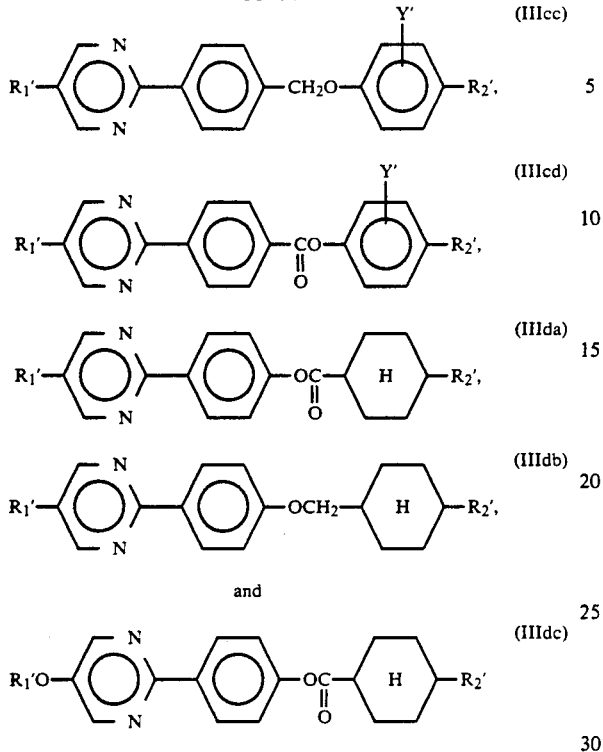
In the above-mentioned formula (IV), more preferred compounds thereof may include those represented by the formulas (IVaa) to (IVcd):
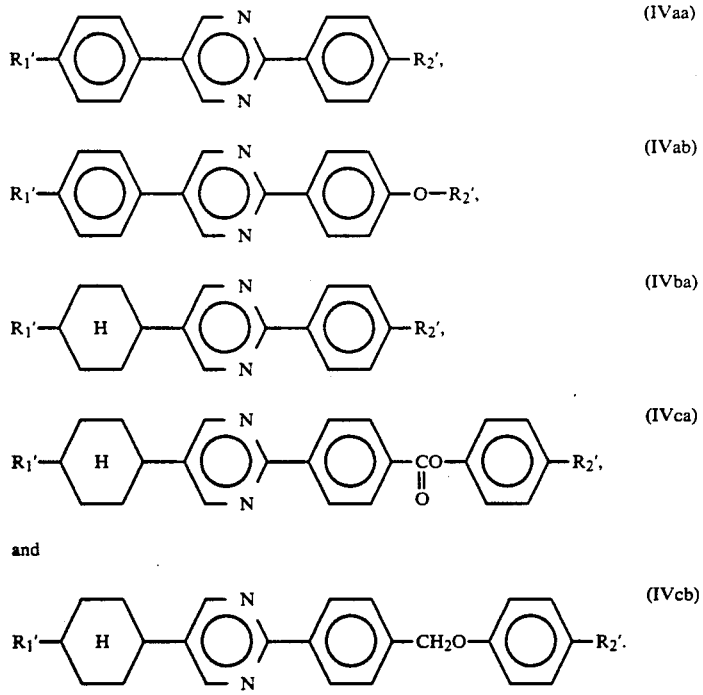
and
In the above-mentioned formula (V), more preferred compounds thereof may include those represented by the formulas (Vaa) to (Vbf):
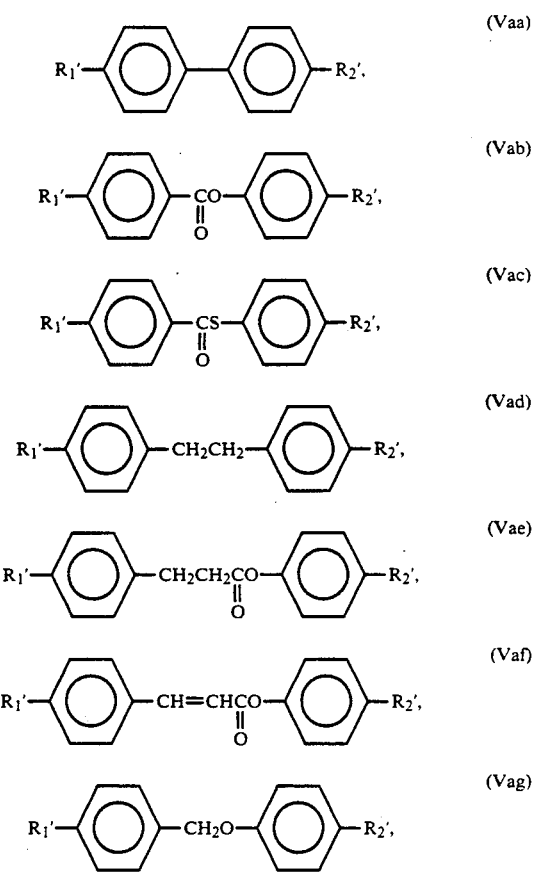
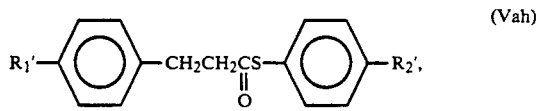

-continued

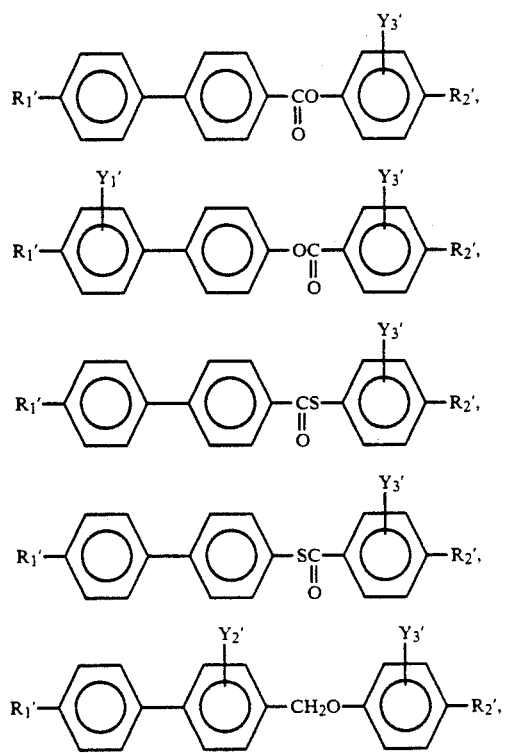

and

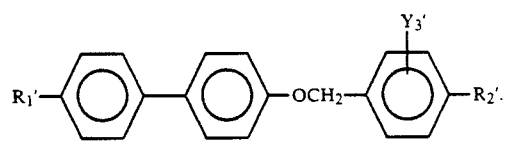

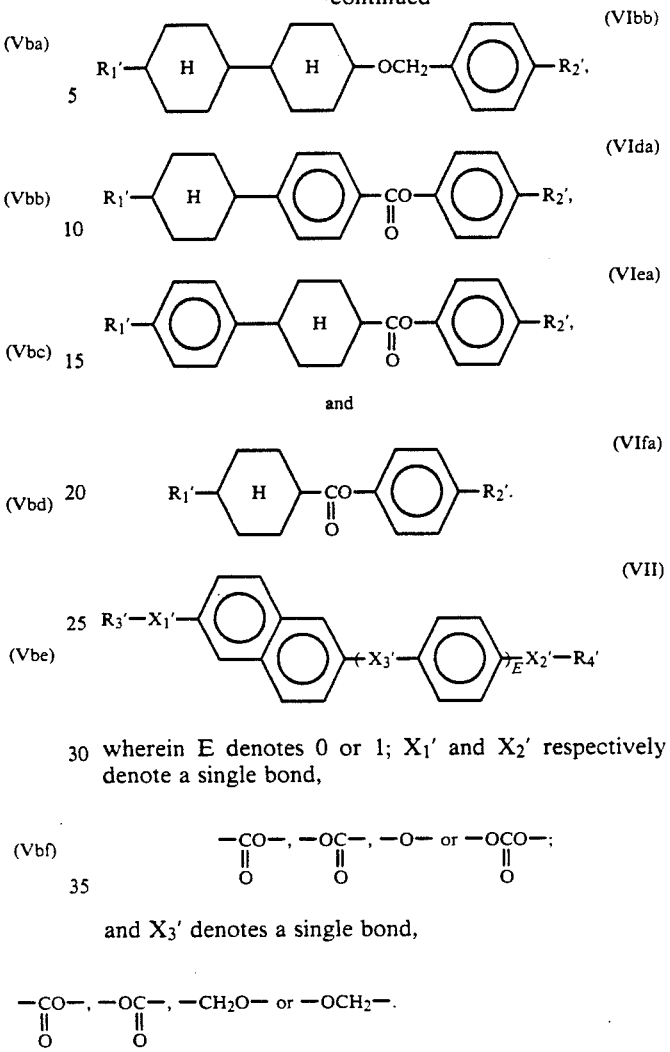

and

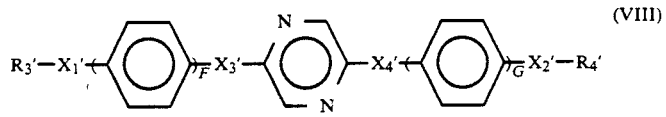

wherein E denotes 0 or 1; $X_1'$ and $X_2'$ respectively denote a single bond, $$-\underset{\underset{O}{\|}}{C}O-, -O\underset{\underset{O}{\|}}{C}-, -O- \text{ or } -O\underset{\underset{O}{\|}}{C}O-;$$

and $X_3'$ denotes a single bond, $$-\underset{\underset{O}{\|}}{C}O-, -O\underset{\underset{O}{\|}}{C}-, -CH_2O- \text{ or } -OCH_2-.$$

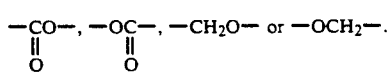

wherein F and G respectively denote 0 or 1; $X_1'$ and $X_2'$ respectively denote a single bond, $$-\underset{\underset{O}{\|}}{C}O-, -O\underset{\underset{O}{\|}}{C}- \text{ or } -O-;$$

and $X_3'$ and $X_4'$ respectively denote a single bond, $$-\underset{\underset{O}{\|}}{C}O-, -O\underset{\underset{O}{\|}}{C}-, -CH_2O- \text{ or } -OCH_2-.$$

In the above formula (VII), preferred compounds thereof may include those represented by the following formulas (VIIa) and (VIIb):

In the above-mentioned formula (VI), more preferred compounds thereof may include those represented by the formulas (VIaa) to (VIfa):

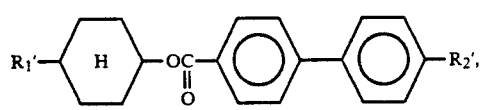

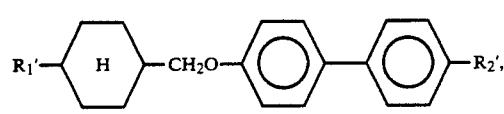

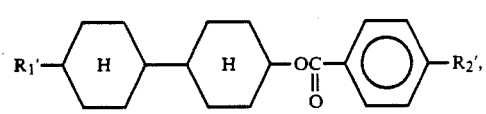

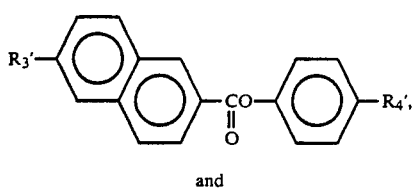 (VIIa)

and

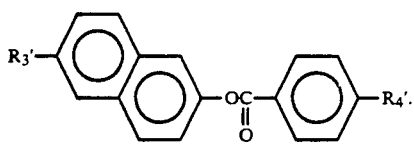 (VIIb)

In the above formula (VIII), preferred compounds thereof may include those represented by the following formulas (VIIIa) and (VIIIb).

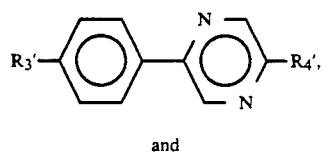 (VIIIa)

and

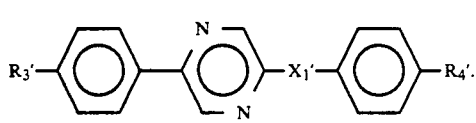 (VIIIb)

More preferred compounds of the formula (VIII) may include those represented by the formulas (VIIIaa) to (VIIIbb):

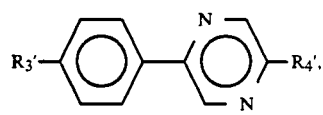 (VIIIaa)

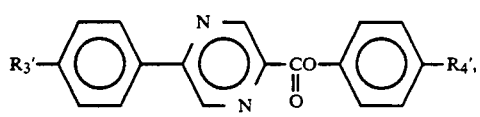 (VIIIba)

and

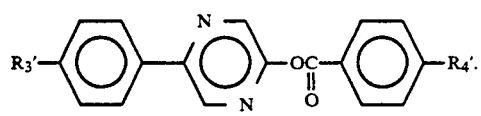 (VIIIbb)

Herein, $R_3'$ and $R_4'$ respectively denote a linear or branched alkyl group having 1-18 carbon atoms capable of including one or non-neighboring two or more methylene groups which can be replaced with —CH halogen- and capable of further including one or two or more non-neighboring methylene groups other than those directly connected to $X_1'$ or $X_2'$ which can be replaced with at least one species of

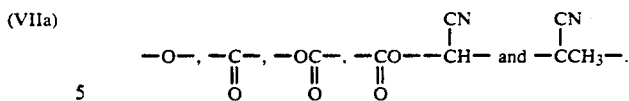

with proviso that $R_3'$ and $R_4'$ respectively do not connect to a ring structure by a single bond when $R_3'$ and $R_4'$ respectively denote a halogenated alkyl group containing one methylene group replaced with —CH halogen-.

Further, preferred examples of $R_3'$ and $R_4'$ may respectively include those represented by the following groups (i) to (vii):

i) linear alkyl group having 1-15 carbon atoms;

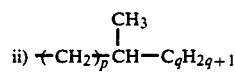

wherein p denotes an integer of 0-5 and q denotes an integer of 2-11 (optically active or inactive);

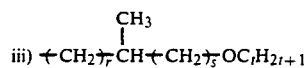

wherein r denotes an integer of 0-6, s denotes 0 or 1, and t denotes an integer of 1-14 (optically active or inactive);

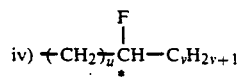

wherein u denotes an integer of 0 or 1 and v denotes an integer of 1-16;

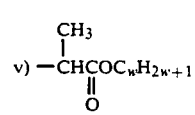

wherein w denotes an integer of 1-15 (optically active or inactive);

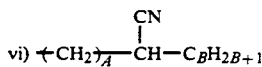

wherein A denotes an integer of 0-2 and B denotes an integer of 1-15 (optically active or inactive); and

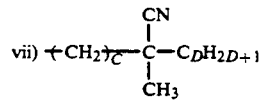

wherein C denotes an integer of 0-2 and D denotes an integer of 1-15 (optically active or inactive).

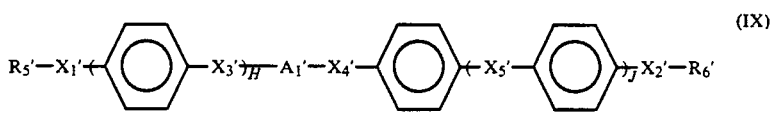 (IX)

wherein H and J respectively denote 0 or 1 with proviso that H+J=0 or 1; $X_1'$ and $X_2'$ respectively denote a single bond, —CO—, —OC— or —O—;
  ‖         ‖
  O         O $A_1'$ denotes

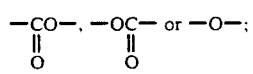

—CO—, —OC—, —CH₂O— or —OCH₂—.
  ‖         ‖
  O         O

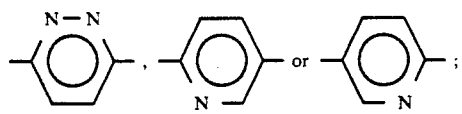 (X)

wherein $X_1'$ and $X_2'$ respectively denote a single bond,

—CO—, —OC— or —O—;
  ‖         ‖
  O         O $A_2'$ denotes

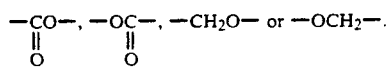

and $X_3'$ and $X_4'$ respectively denote a single bond,

—CO—, —OC—, —CH₂O— or —OCH₂—.
  ‖         ‖
  O         O

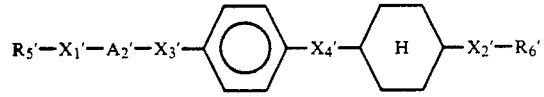 (XI)

wherein $X_1'$ and $X_2'$ respectively denote a single bond,

—CO—, —OC— or —O—;
  ‖         ‖
  O         O $A_3'$ denotes

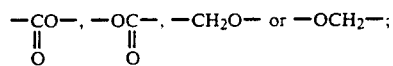

and $X_3'$ respectively denotes a single bond

—CO—, —OC—, —CH₂O— or —OCH₂—.
  ‖         ‖
  O         O

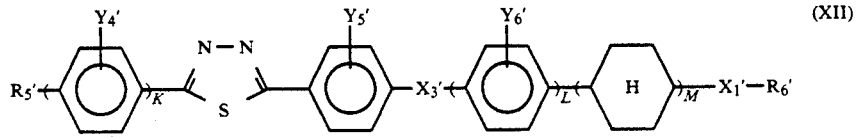 (XII)

wherein K L and M respectively denote 0 or 1 with the proviso that K+L+M=0 or 1; $X_1'$ denotes a single bond, —CO—, —OC— or —O—;
  ‖         ‖
  O         O $X_3'$ denotes a single bond, —CO—, —OC—, —CH₂O— or —OCH₂—;
  ‖         ‖
  O         O and $Y_4'$, $Y_5'$ and $Y_6'$ respectively denote H or F.

In the above formula (IX), preferred compounds thereof may include those represented by the following formulas (IXa) to (IXc):

 (IXa)

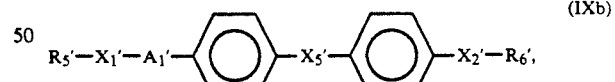 (IXb)

and

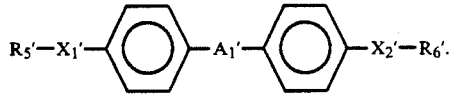 (IXc)

In the above formula (X), preferred compounds thereof may include those represented by the following formulas (Xa) and (Xb):

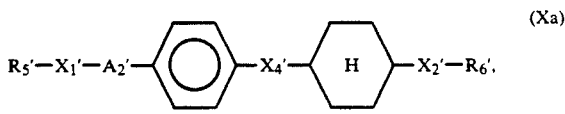 (Xa)

-continued $$R_5'-X_1'-A_2'-X_3'-\underset{}{\bigcirc}-\underset{H}{\bigcirc}-X_2'-R_6'. \quad (Xb)$$

In the above formula (XII), preferred compounds thereof may include those represented by the following formulas (XIIa) and (XIId):

(XIIa)

(XIIb)

(XIIc)

and (XIId)

In the above-mentioned formula (IX), more preferred compounds thereof may include those represented by the formulas (IXaa) to (IXcc):

(IXaa)

(IXab)

(IXac)

(IXad)

(IXba)

(IXbb)

(IXbc)

(IXbd)

(IXbe)

(IXca)

(IXcb)

and (IXcc)

In the above-mentioned formula (X), more preferred compounds thereof may include those represented by the formulas (Xaa) to (Xbb):

(Xaa)

(Xab)

(Xac)

(Xba)

and (Xbb)

In the above formula (XI), preferred compounds thereof may include those represented by the following formulas (XIa) to (XIg):

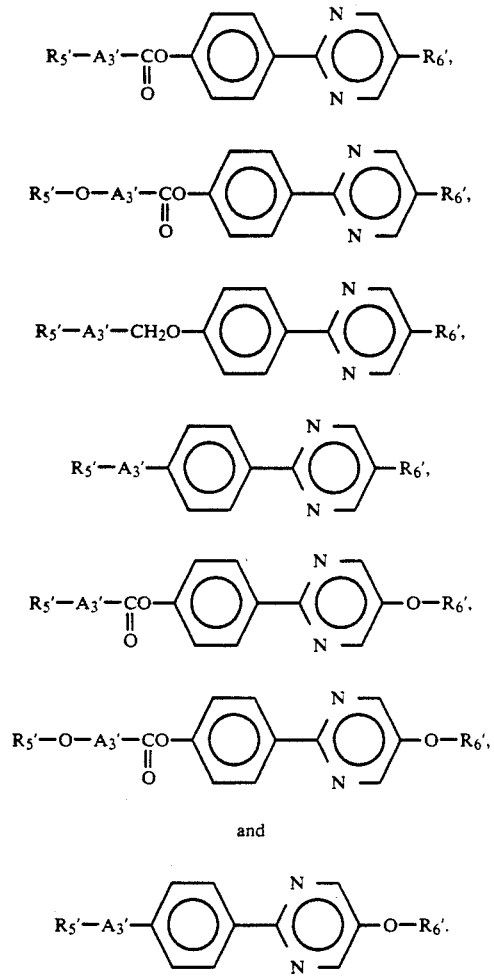

and

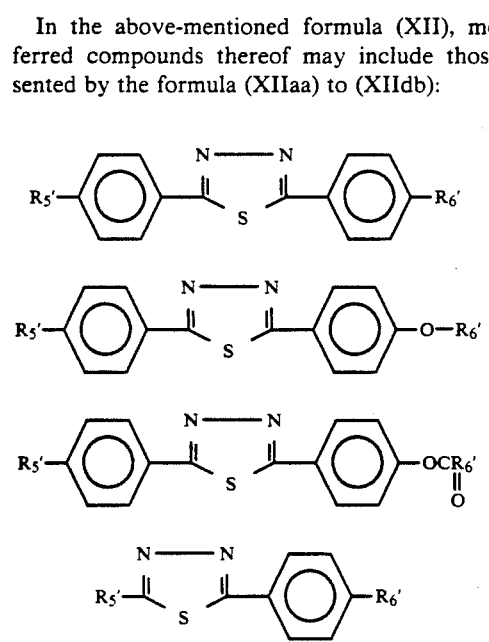

In the above-mentioned formula (XII), more preferred compounds thereof may include those represented by the formula (XIIaa) to (XIIdb):

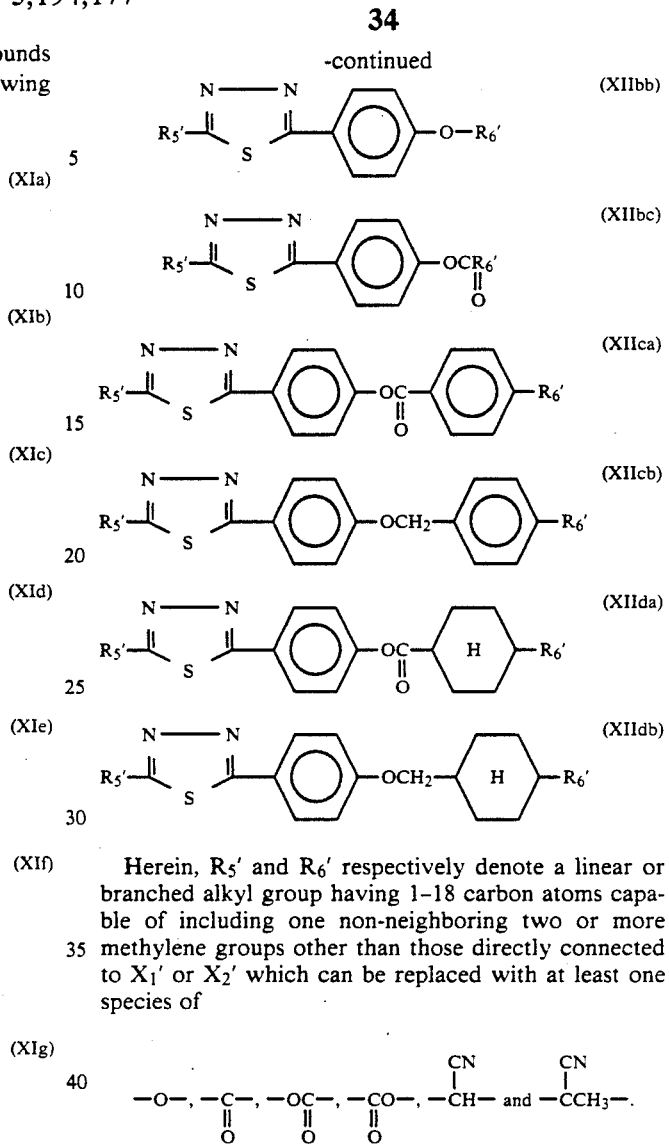

Herein, $R_5'$ and $R_6'$ respectively denote a linear or branched alkyl group having 1-18 carbon atoms capable of including one non-neighboring two or more methylene groups other than those directly connected to $X_1'$ or $X_2'$ which can be replaced with at least one species of $$-O-, -\underset{\underset{O}{\|}}{C}-, -O\underset{\underset{O}{\|}}{C}-, -\underset{\underset{O}{\|}}{C}O-, -\underset{\underset{CN}{|}}{C}H- \text{ and } -\underset{\underset{CN}{|}}{C}CH_3-.$$

Further, preferred examples of $R_5'$ and $R_6'$ may respectively include those represented by the following groups (i) to (vi):

i) a linear alkyl group having 1-15 carbon atoms;

ii) 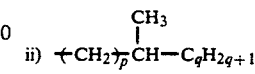

wherein p denotes an integer of 0-5 and q denotes an integer of 2-11 (optically active or inactive);

iii) 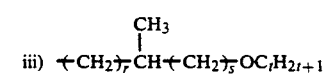

wherein r denotes an integer of 0-6, s denotes 0 or 1, and t denotes an integer of 1-14 (optically active or inactive);

iv) 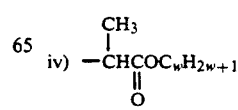

wherein w denotes an integer of 1-15 (optically active or inactive);

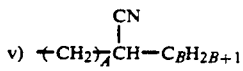
v) $\text{+CH}_2\text{)}_A\text{CH}-\text{C}_B\text{H}_{2B+1}$ with CN substituent wherein A denotes an integer of 0-2 and B denotes an integer of 1-15 (optically active or inactive); and

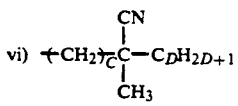
vi) $\text{+CH}_2\text{)}_C\text{C}-\text{C}_D\text{H}_{2D+1}$ with CN and CH$_3$ substituents wherein C denotes an integer of 0-2 and D denotes an integer of 1-15 (optically active or inactive).

In formulating the liquid crystal composition according to the present invention, the liquid crystal composition may desirably contain 1-80 wt. %, preferably 1-60 wt. %, more preferably 1-40 wt. % of an optically active compound represented by the formula (I).

Further, when two or more species of the compounds represented by the formula (I) are used, the liquid crystal composition may desirably contain 1-80 wt. %, preferably 1-60 wt. %, more preferably 1-40 wt. %, of the two or more species of the compounds represented by the formula (I).

The liquid crystal device according to the present invention may preferably be prepared by heating the liquid crystal composition assuming a chiral smectic phase prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity prepared as described above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2-10 wt. %, by spinner coating dip coating, screen printing, spray coating or roller coating, followed by curing or hardening under prescribed hardening condition (e.g., by heating). The insulating alignment control layer may have a thickness of ordinarily 50 Å-1 micron, preferably 100-3000 Å, further preferably 100-1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a liquid crystal assuming a chiral smectic phase is sealed up to provide a liquid crystal layer 1 in a thickness of generally 0.5 to 20 microns, preferably 1 to 5 microns.

The liquid crystal provided by the composition of the present invention may desirably comprise a SmC* phase (chiral smectic C phase) in a wide temperature range including room temperature (particularly, broad in a lower temperature side) and also shows high-speed responsiveness, a smaller temperature-dependence of response speed and wide drive voltage margin when contained in a device.

Particularly, in order to show a good alignment characteristic to form a uniform monodomain, the ferroelectric liquid crystal may show a phase transition series comprising isotropic phase—Ch phase (cholesteric phase)—SmA phase (smectic A phase)—SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
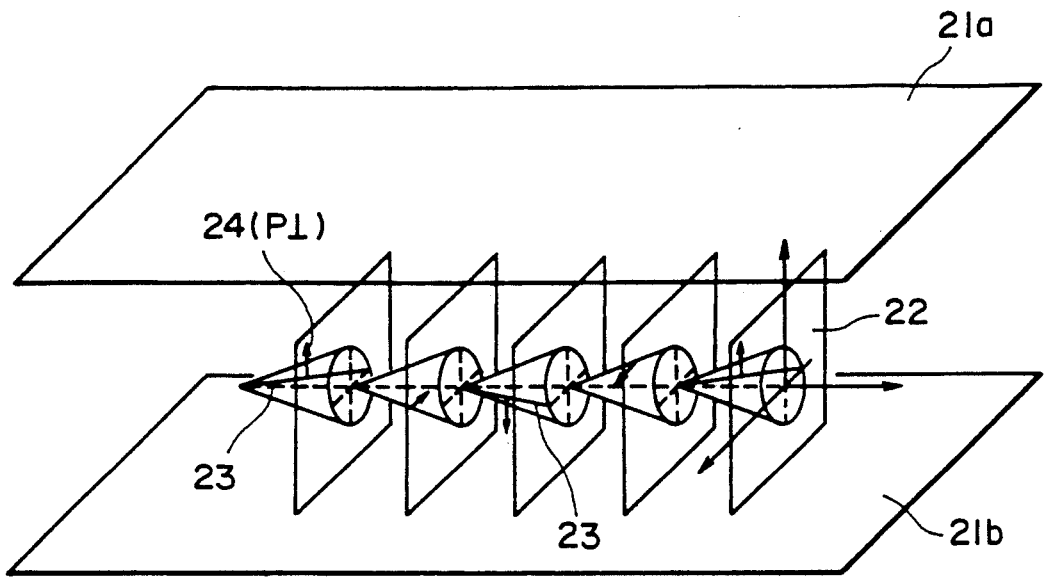
FIGS. 2 and 3 are schematic perspective views of a device cell embodiment for illustrating the operation principle of a liquid crystal device utilizing ferroelectricity of a liquid crystal composition.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment ($P_\perp$) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments ($P_\perp$) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
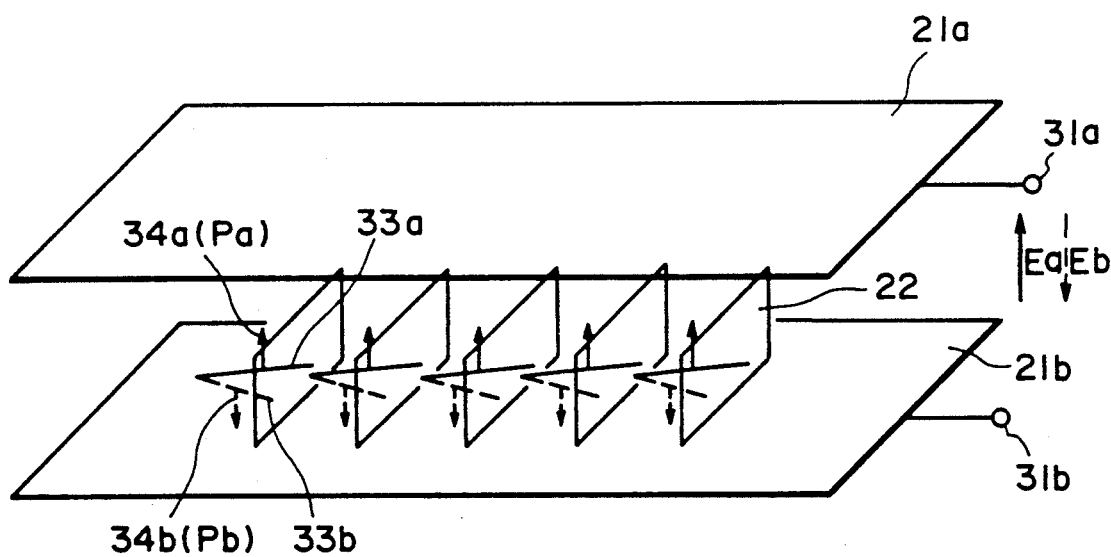

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 4:
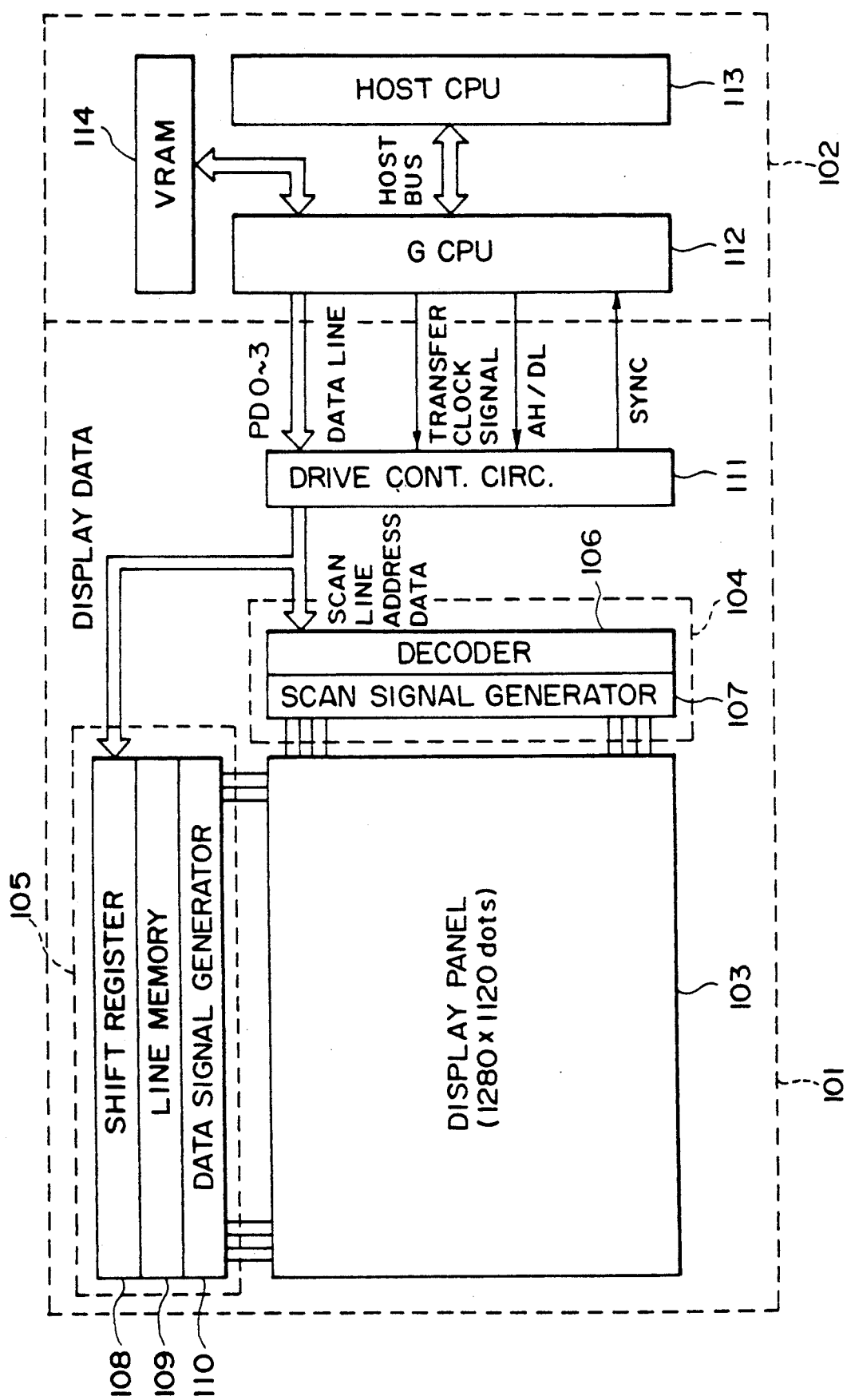
FIG. 4 is a block diagram showing a display apparatus comprising a liquid crystal device utilizing ferroelectricity of a liquid crystal composition and a graphic controller.
Figure 5:
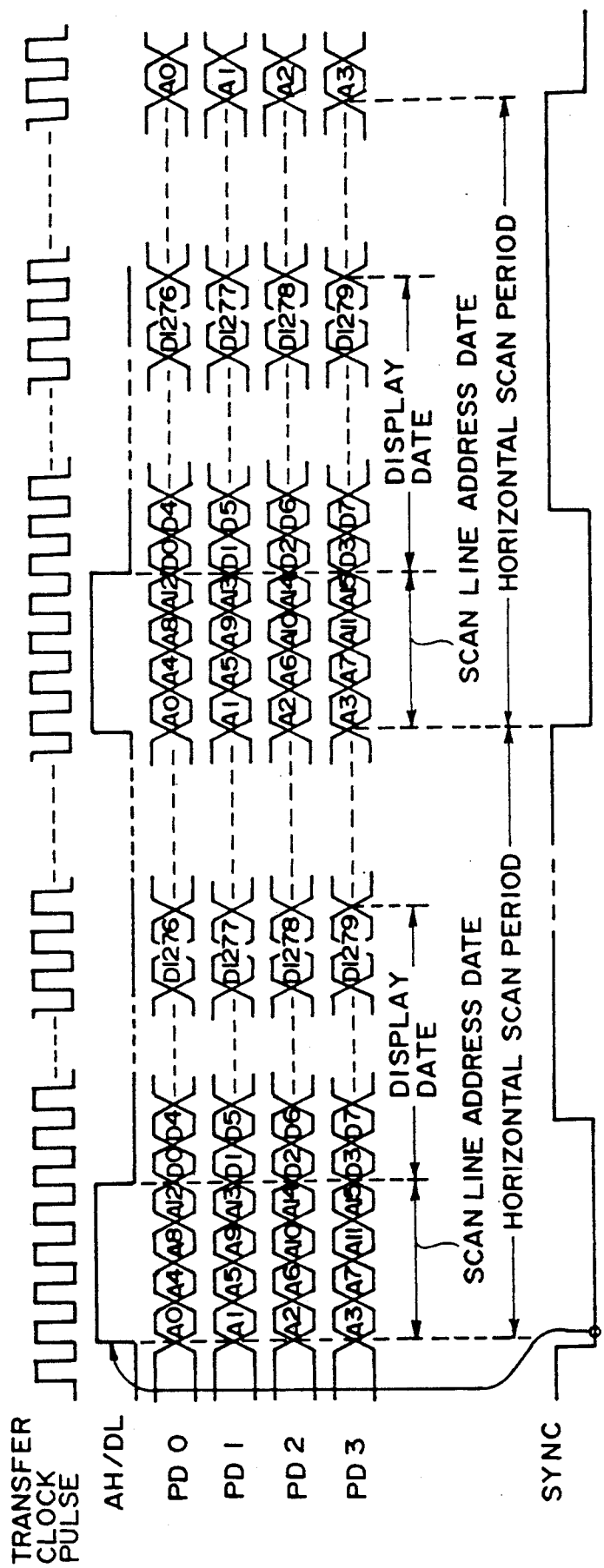
FIG. 5 is a time chart of image data communication showing time correlation between signal transfer and driving with respect to a liquid crystal display apparatus and a graphic controller.

Based on the arrangement and data format comprising image data accompanied with scanning line address data and by adopting communication synchronization using a SYNC signal as shown in FIGS. 4 and 5, there is provided a liquid crystal display apparatus of the present invention which uses the liquid crystal device according to the present invention as a display panel portion.

Referring to FIG. 4, the ferroelectric liquid crystal display apparatus 101 includes a graphic controller 102, a display panel 103, a scanning line drive circuit 104, a data line drive circuit 105, a decoder 106, a scanning signal generator 107, a shift resistor 108, a line memory 109, a data signal generator 110, a drive control circuit 111, a graphic central processing unit (GCPU) 112, a host central processing unit (host CPU) 113, and an image data storage memory (VRAM) 114.

Image data are generated in the graphic controller 102 in an apparatus body and transferred to a display panel 103 by signal transfer means shown in FIGS. 4 and 5. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control of the display apparatus is principally realized in the graphic controller 102. A light source is disposed at the back of the display panel 103.

The optically active compound of the present invention may be contained in a nematic liquid crystal composition, thus providing a liquid crystal composition showing uniform nematic phase free from reverse domain.

Hereinbelow, the present invention will be explained more specifically with reference to examples. It is however to be understood that the present invention is not restricted to these examples.

EXAMPLE 1

Optically active 2-[4-(1-trifluoromethylheptyloxymethyl)phenyl]-6-hexaloxybenzothiazole (Example Compound No. 64) was synthesized through the following steps i)–iv) according to the above-mentioned reaction scheme A.

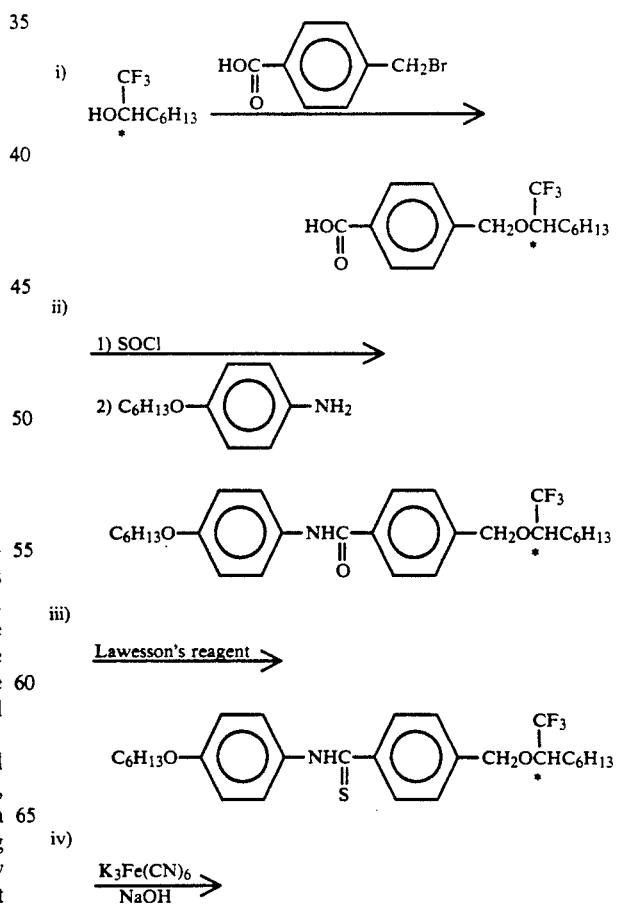

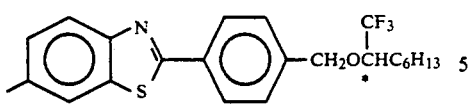

Step i) Production of optically active 4-(1-trifluoromethylheptyloxymethyl)benzoic acid A solution of 2.0 g (10.9 mM) of optically active 1,1,1-trifluoro-2-octanol in 6 ml of dry tetrahydrofuran (THF) was added to a solution of 2.33 g (10.9 mM) of 4-bromomethylbenzoic acid in 6 ml of dry dimethyl sulfoxide (DMSO).

Then, the above mixture was cooled on an ice bath. 1.31 g (32.7 mM) of 60 %-sodium hydride was washed with hexane and dispersed in 5 ml of DMSO. The dispersion was added to the above mixture, followed by stirring for several hours and further stirring overnight after addition of 40 ml of THF. After the reaction, 20 ml of water, 6 ml of 3M-hydrochloric acid and common salt were added to the reaction mixture, followed by extraction with 20 ml of diethyl ether. The resultant organic layer was dried with anhydrous magnesium sulfate, followed by distilling-off of the solvent and purification by silica gel column chromatography (eluent: hexane/ethyl acetate =4/3) to obtain 2.36 g (7.41 mM) of objective optically active 4-(1-trifluoromethylheptyloxymethyl)benzoic acid (Yield: 68 %).

Step ii) Production of 4'-hexyloxy-4-(1-trifluoromethylheptyloxymethyl)thiobenzanilide.

To 0.8 g (2.5 mM) of optically active 4-(1-trifluoromethylheptyloxymethyl)benzoic acid, 5 ml of thionyl chloride was added, followed by refluxing for 1 hour. After the reflux, an excessive thionyl chloride was distilled off under reduced pressure. To the resultant chloride, 0.52 g (2.7 mM) of 4-hexyloxyaniline and a mixture solution of 0.25 g (3.2 mM) of pyridine and 10 ml of dry dioxane were added, followed by stirring for 30 minutes. After the reaction, cold water was added to the reaction mixture, followed by filtration to obtain a crude crystal. The crude crystal was recrystallized from a mixture solvent (water/methanol) to obtain 1.0 g (2.0 mM) of an objective product (Yield: 81%).

Step iii) Production of optically active 4'-hexyloxy-4-(1-trifluoromethylheptyloxymethyl)thiobenzanilide.

0.98 g (1.99 mM) of optically active 4'-hexyloxy-4-(1-trifluoromethylheptyloxymethyl)thiobenzanilide, 0.97 g (2.39 mM) of Lawesson's reagent and 10 ml of THF were stirred for 1.5 hours at 75° C. After the reaction, water was added to the reaction mixture, followed by extraction with toluene, drying with anhydrous sodium sulfate and distilling-off of the solvent to obtain a crude product. The crude product was purified by silica gel column chromatography (eluent: toluene) to obtain 1.0 g (1.96 mM) of an objective product (Yield: 98%).

Step iv) Production of optically active 2-[4-(1-trifluoromethylheptyloxymethyl)phenyl]-6-hexyloxybenzothiazole.

1.0 g (1.96 mM) of optically active 4'- hexyloxy-4-(1-trifluoromethylheptyloxymethyl)thiobenzanilide and 1.70 g (3.9 mM) of 90%-sodium hydroxide were dissolved in 15 ml of methanol. To the solution, 5 ml of an aqueous solution of 1.61 g (4.9 mM) of potassium ferricyanide was added dropwise, followed by stirring for 1 hour at room temperature. After the reaction, water was added to the reaction mixture, followed by filtration to obtain a crude crystal. The crude crystal was purified by silica gel column chromatography (eluent: toluene/hexane=1/2) and recrystallized two times from ethanol to obtain 0.49 g (0.97 mM) of optically active 2-[4-(1-trifluoromethylheptyloxymethyl)phenyl]-6-hexyloxybenzothiazole (Yield: 49%, m.p.=69.1° C.).

EXAMPLE 2

Optically active 2-[4-(1-trifluoromethylheptyloxymethyl)phenyl]-6-oxtylbenzothiazole (Example Compound No. 24) was synthesized through the following steps i)-iii) according to the above-mentioned reaction scheme B.

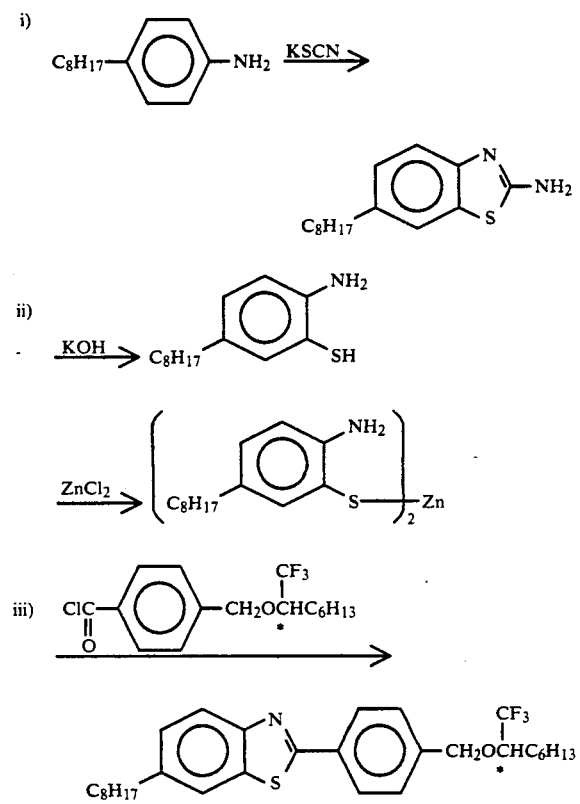

Step i) Production of 2-amino-6-octylbenzothiazole

In a 2 liters-reaction vessel, 50.0 g (0.24M) of p-octylaniline, 47.3 g (0.49M) of potassium thiocyanate and 350 ml of acetic acid were placed and cooled below 10° C. Under intersive stirring, a solution of 39.0 g of bromine in 120 ml of acetic acid was added dropwise to the above mixture in 75 minutes below 10° C., followed by reaction for 2 hours below 10° C. After the reaction, 500 ml of water was added to the reaction mixture and heated to dissolve the precipitate, followed by filtration under heating. Ammonia water was added to the filtrate so as to provide a basic solution, followed by cooling on an iced bath to precipitate a crystal. The crystal was recovered by filtration, followed by washing with water and drying to obtain a crude product. The crude product was purified by silica gel column chromatography (eluent: n-hexane/ethyl acetate) to obtain 41.2 g of 2-amino-6-octylbenzothiazole (Yield: 68%).

Step ii) Production of zinc 5-octyl-2-aminobenzenethiol.

In a 1 liter-reaction vessel, 35.0 g (0.14M) of 2-amino-6-octylbenzothiazole, 150 ml of water and 150 g of KOH were placed and heat-refluxed for 20 hours. After cooling, ethanol was added to the above mixture to dissolve the crystal. To the resultant solution, 5N-acetic acid aqueous solution was added dropwise so as to provide a pH value of 9 to precipitate a crystal. The crystal was recovered by filtration and a solution of 9.8 g of $ZnCl_2$ in 44 ml of 15%-acetic acid aqueous solution was added dropwise to the filtrate. After the addition, the mixture was heated for 1 hour at 80° C., followed by filtration to recover a crystal. The crystal was successively washed with hot water, ethanol and water and dried to obtain 25.0 g of zinc 5-octyl-2-aminobenzenethiol (Yield: 66%).

Step iii) Production of optically active 2-[4-(1-trifluoromethylheptyloxymethyl)phenyl]-6-octylbenzothiazole To 0.5 g (1.6 mM) of optically active 4-(1-trifluoromethylheptyloxymethyl)benzoic acid, 5 ml of thionyl chloride was added, followed by refluxing for 1 hour. After the reflux, an excessive thionyl chloride was distilled off under reduced pressure. To the acid chloride, 0.41 g (0.8 mM) of zinc 5-octyl-2-aminobenzenethiol was added, followed by stirring for 30 minutes at 200° C. After the reaction, the reaction mixture was left standing for cooling. To the reaction mixture, 8 ml of a dilute sodium hydroxide aqueous solution was added, followed by extraction with ethyl acetate. After washing with water, the extract was dried with anhydrous magnesium sulfate, followed by distilling-off of the solvent and purification by silica gel column chromatography (eluent: hexane/ethyl acetate=50/1) to obtain a crystal. The crystal was treated with activated carbon and recrystallized from ethanol to obtain 0.33 g of optically active 2-[4-(1-trifluoromethylheptyloxymethyl)-phenyl]-6-octylbenzothiazole (Yield: 41%, m.p.=37.2° C.).

EXAMPLE 3

Optically active 2-[4-(1-trifluoromethylheptyloxymethyl)phenyl]-6-(2-fluorooctyloxy)benzothiazole (Example Compound No. 98) was synthesized in the same manner as in Example 1 through the following steps.

EXAMPLE 4

A liquid crystal composition A was prepared by mixing the following compounds in the respectively indicated proportions.

| Structural formula | wt. parts |
|---|---|
| $C_6H_{13}O$—⟨phenyl⟩—⟨pyrimidine(N,N)⟩—$C_8H_{17}$ | 48.57 |
| $C_9H_{19}O$—⟨phenyl⟩—⟨pyrimidine(N,N)⟩—$C_8H_{17}$ | 24.29 |
| $C_8H_{17}O$—⟨phenyl⟩—⟨pyrimidine(N,N)⟩—$C_{10}H_{21}$ | 12.14 |
| $C_3H_7$—⟨cyclohexyl-H⟩—CO-O—⟨phenyl⟩—⟨pyrimidine(N,N)⟩—$C_{11}H_{23}$ | 3.75 |
| $C_4H_9$—⟨cyclohexyl-H⟩—CO-O—⟨phenyl⟩—⟨pyrimidine(N,N)⟩—$C_{11}H_{23}$ | 3.75 |
| $C_5H_{11}$—⟨cyclohexyl-H⟩—CO-O—⟨phenyl⟩—⟨pyrimidine(N,N)⟩—$C_{11}H_{23}$ | 7.50 |

The liquid crystal composition A was further mixed with the following Example Compound No. 64 prepared in Example 1 in the proportions indicated below to provide a liquid crystal composition B.

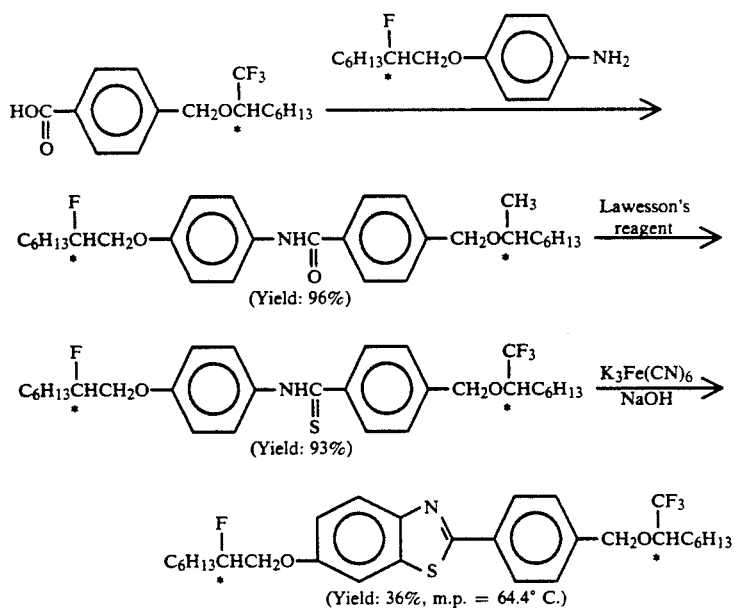

| Ex. Comp. No. | Structural formula | wt. parts |
|---|---|---|
| 64 |  | 5 |
| | Composition A | 95 |

The liquid crystal composition B showed the following phase transition series.

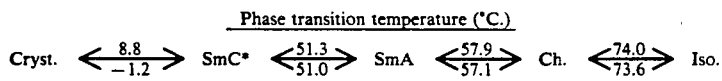

Herein, the respective symbols denote the following phase:
Iso.: isotropic phase,
Ch.: cholesteric phase,
SmA: smectic A phase,
SmC*: chiral smectic C phase, and
Cryst.: crystal.

EXAMPLE 5

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K. K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then, each of the liquid crystal composition B prepared in Example 4 was heated into an isotropic liquid, and injected into the above prepared cell under vacuum and, after sealing, was gradually cooled at a rate of 20° C./hour to 25° C. to prepare a ferroelectric liquid crystal device.

Each of the ferroelectric liquid crystal devices was subjected to measurement of the magnitude of spontaneous polarization Ps and an optical response time (time from voltage application until the transmittance change reaches 90% of the maximum under the application of a peak-to-peak voltage Vpp of 20 V in combination with right-angle cross-nicol polarizers).

The results are shown below.

| | 30° C. | 40° C. | 45° C. |
|---|---|---|---|
| Response time (μsec) | 133 | 93 | 73 |
| Ps (nC/cm²) | 6.5 | 4.6 | 3.2 |

EXAMPLE 6

A liquid crystal composition C was prepared by mixing the following Example Compound No. 24 prepared in Example 2 in the indicated proportions with the liquid crystal composition A prepared in Example 4.

| Ex. Comp. No. | Structural formula | wt. parts |
|---|---|---|
| 24 |  | 5 |
| | Composition A | 95 |

The liquid crystal composition C showed the following phase transition series.

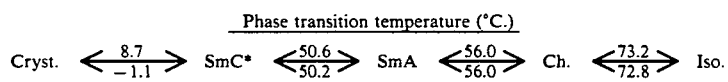

A ferroelectric liquid crystal device was prepared in the same manner as in Example 5 except for using the composition C. The ferroelectric liquid crystal device was subjected to measurement of the magnitude of spontaneous polarization Ps and response time in the same manner as in Example 5, whereby the following results were obtained.

| | 30° C. | 40° C. | 45° C. |
|---|---|---|---|
| Response time (μsec) | 120 | 83 | 63 |
| Ps (nC/cm²) | 6.4 | 4.5 | 3.0 |

EXAMPLE 7

A liquid crystal composition D was prepared by mixing the following Example Compound No. 98 prepared in Example 3 in the indicated proportions with the liquid crystal composition A prepared in Example 4.

| Ex. Comp. No. | Structural formula | wt. parts |
|---|---|---|
| 98 | 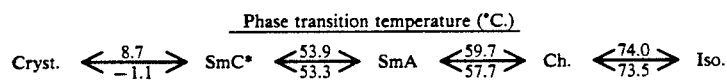 | 5 |
| | Composition A | 95 |

The liquid crystal composition D showed the following phase transition series.

Phase transition temperature (°C.)

Cryst. $\xleftrightarrow{\;8.7\;}_{-1.1}$ SmC* $\xleftrightarrow{\;53.9\;}_{53.3}$ SmA $\xleftrightarrow{\;59.7\;}_{57.7}$ Ch. $\xleftrightarrow{\;74.0\;}_{73.5}$ Iso.

A ferroelectric liquid crystal device was prepared in the same manner as in Example 5 except for using the composition D. The ferroelectric liquid crystal device was subjected to measurement of the magnitude of spontaneous polarization Ps and response time in the same manner as in Example 5, whereby the following results were obtained.

| | 30° C. | 40° C. | 45° C. |
|---|---|---|---|
| Response time (μsec) | 131 | 92 | 76 |
| Ps (nC/cm²) | 6.8 | 5.6 | 4.2 |

EXAMPLE 8

Two glass plates were provided respectively coated with an ITO film to form a transparent electrode, which was further coated with a solution of polyimide resin precursor (SP-510, available from Toray K.K.) by a spinner coater to obtain a polyimide film. Each coating film was subjected to rubbing. The thus treated two glass plates were applied each other so that their rubbed directions were at right angles to each other to form a blank cell with a cell gap of 8 microns.

A nematic liquid crystal composition (Lixon GR-63 (biphenyl liquid crystal mixture), available from Chisso K.K.) was injected into the above-prepared cell to prepare a TN-type liquid crystal device (or cell).

When the TN-type liquid crystal device was subjected to observation with a polarizing microscope (magnifying power of 10), occurrence of a reverse domain or twist disclination (i.e., a striped pattern) was recognized.

On the other hand, a TN-type liquid crystal device was prepared by mixing 1 wt. part of a mesomorphic compound (Ex. Comp. No. 64) prepared in Example 1 according to the present invention with 99 wt. parts of the above-mentioned nematic liquid crystal composition (Lixon GR-63), and injected into a blank cell to provide a TN-type liquid crystal device in the same manner as described above.

When the device was subjected to observation with a polarizing microscope, uniform nematic phase free from reverse domain was observed.

As described hereinabove, according to the present invention, there is provided an optically active compound with large spontaneous polarization. The compound is effective for providing a liquid crystal composition showing chiral smectic phase to constitute a liquid crystal device using the composition having ferroelectricity. The thus prepared ferroelectric liquid crystal device containing the composition shows a good switching characteristic, an improved low-temperature operation characteristic and a decreased temperature-dependence of response speed. The compound of the present invention is also effective for suppressing occurrence of reverse domain when mixed with a nematic liquid crystal composition. The present invention further provides a display apparatus and a display method which employ such a device as a display unit, whereby good display characteristics can be obtained in combination with a light source, a drive circuit, etc.

What is claimed is:

1. An optically active compound represented by the following formula (I):

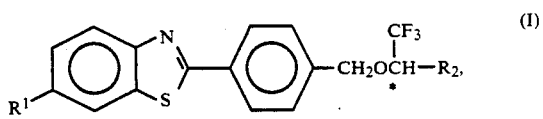

wherein $R_1$ denotes a linear or branched alkyl group having 1-18 carbon atoms optionally including one or non-neighboring two or more methylene groups which can be replaced with —X— or

with the proviso that X denotes O or S and Y denotes halogen; $R_2$ denotes a linear alkyl group having 4-8 carbon atoms: and C* denotes an optically active asymmetric carbon atom.

2. A compound according to claim 1, wherein $R_1$ denotes any one of the following groups (i) to (iv):

(i) —G—$C_aH_{2a+1}$—n wherein G denotes a single bond, —O— or —S—; and a is an integer of 1-18;

(ii)

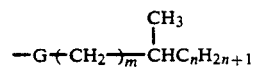

wherein G denotes a single bond, —O— or —S—; m is an integer of 0-7 and n is an integer of 1-9;

(iii)

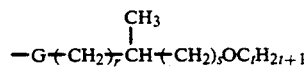

wherein G denotes a single bond, —O— or —S—; r is an integer of 0-7; s is 0 or 1 and t is an integer of 1-14; and (iv)

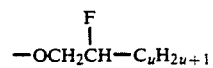

wherein u is an integer of 1-16.

3. A compound according to claim 1, wherein $R_2$ denotes a linear alkyl group having 4-6 carbon atoms.

4. A liquid crystal composition comprising at least two compounds, at least one of which is an optically active compound of the formula (I) according to claim 1.

5. A liquid crystal composition according to claim 4, which comprises 1-80 wt. % of a compound of the formula (I).

6. A liquid crystal composition according to claim 4, which comprises 1-60 wt. % of a compound of the formula (I).

7. A liquid crystal composition according to claim 4, which comprises 1-40 wt. % of a compound of the formula (I).

8. A liquid crystal composition according to claim 4, which has a chiral smectic phase.

9. A liquid crystal composition according to claim 4, which has a nematic phase.

10. A liquid crystal device, comprising a pair of electrode plates and a liquid crystal composition according to claim 4 disposed between the electrode plates.

11. A liquid crystal device according to claim 10, which further comprises an insulating alignment control layer.

12. A liquid crystal device according to claim 11, wherein the insulating alignment control layer has been subjected to rubbing.

13. A liquid crystal device according to claim 10, wherein the liquid crystal composition is disposed in a thickness suppressing formation of a helical structure of liquid crystal molecules between the electrode plates.

14. A display apparatus comprising a liquid crystal device according to claim 10, and voltage application means for driving the liquid crystal device.

15. A display apparatus according to claim 14, wherein the liquid crystal device constitutes a display panel wherein the alignment direction of liquid crystal molecules is switched by utilizing ferroelectricity of the liquid crystal composition to effect display.

16. A display apparatus according to claim 14, which further comprises a light source.

17. A display method, comprising:
providing a liquid crystal composition comprising at least two mesomorphic compound, at least one of which is an optically active compound of the formula (I) according to claim 1; and
switching the alignment direction of liquid crystal molecules by applying voltages to the liquid crystal composition to effect display.

18. A display method according to claim 17, wherein $R_1$ in the formula (I) denotes any one of the following groups (i) to (iv):
(i) —G—$C_aH_{2a+1}$—n wherein G denotes a single bond, —O— or —S—; and a is an integer of 1-18;
(ii)

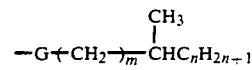

wherein G denotes a single bond, —O— or —S—; m is an integer of 0-7 and n is an integer of 1-9;
(iii)

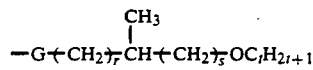

wherein G denotes a single bond, —O— or —S—; r is an integer of 0-7; s is 0 or 1 and t is an integer of 1-14; and
(iv)

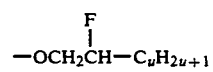

wherein u is an integer of 1-16.

19. A display method according to claim 17, wherein $R_2$ in the formula (I) denotes a linear alkyl group having 4-6 carbon atoms.

20. A display method according to claim 17, wherein the liquid crystal composition comprises 1-80 wt. % of a compound of the formula (I).

21. A display method according to claim 17, wherein the liquid crystal composition comprises 1-60 wt. % of a compound of the formula (I).

22. A display method according to claim 17, wherein the liquid crystal composition comprises 1-40 wt. % of a compound of the formula (I).

23. A display method according to claim 17, wherein the liquid crystal composition has a chiral smectic phase.

24. A displayl method according to claim 17, wherein the liquid crystal composition has a nematic phase.

25. A display method, comprising:
providing a liquid crystal device comprising a pair of electrode plates and a liquid crystal composition disposed therebetween comprising at least two mesomorphic compound, at least one of which is a mesomorphic compound of the formula (I) according to claim 1; and
switching the alignment direction of liquid crystal molecules by applying voltages to the liquid crystal composition disposed between the electrode plates to effect display.

26. A display method according to claim 25, wherein the liquid crystal device further comprises an insulating alignment control layer between the electrode plates.

27. A display method according to claim 26, wherein the insulating alignment control layer has been subjected to rubbing.

28. A display method according to claim 25, wherein the liquid crystal composition is disposed in a thickness suppressing formation of a helical structure of liquid crystal molecules between the electrode plates.

* * * * *

UNITED STATES PATENT AND TRADEMARK OFFICE
CERTIFICATE OF CORRECTION

PATENT NO. : 5,194,177
DATED : March 16, 1993
INVENTOR(S) : HIROYUKI NOHIRA, ET AL.

It is certified that error appears in the above-identified patent and that said Letters Patent is hereby corrected as shown below:

COLUMN 1

Line 10, "composition" should read --composition,--.

COLUMN 2

Line 2, "ia" should read --a--.

COLUMN 3

Line 10, "the" should read --with the--.
   Line 58, "formula (1" should read --formula (1)--.

COLUMN 6

Line 2, "Reaction Scheme A" should read
       --Reaction Scheme B--.

COLUMN 22

Line 4, "xi)" should read --ix)--.

COLUMN 28

Line 15, "linear" should read --a linear--.

COLUMN 30

Line 25, "K" should read --K,--.

COLUMN 31

Line 12, "and" should read --to--.

UNITED STATES PATENT AND TRADEMARK OFFICE
CERTIFICATE OF CORRECTION

PATENT NO. : 5,194,177
DATED : March 16, 1993
INVENTOR(S) : HIROYUKI NOHIRA, ET AL.

It is certified that error appears in the above-identified patent and that said Letters Patent is hereby corrected as shown below:

COLUMN 32

Line 44, Formula (Xaa),
"$R_5' - A_2$" should read --$R_5' - A_2'$--.

COLUMN 34

Line 34, "one" should read --one or--.

COLUMN 35

Line 54, "plate" should read --plate.--.

COLUMN 36

Line 13, "coating" (first occurrence) should read --coating,--.

COLUMN 40

Line 50, "intersive" should read --intensive--.

COLUMN 43

Line 39, "second" should read --seconds--.

COLUMN 45

Line 41, "applied each other" should read --assembled--.

COLUMN 47

Line 49, "compound," should read --compounds,--.

UNITED STATES PATENT AND TRADEMARK OFFICE
CERTIFICATE OF CORRECTION

PATENT NO. : 5,194,177
DATED : March 16, 1993
INVENTOR(S) : HIROYUKI NOHIRA, ET AL.

It is certified that error appears in the above-identified patent and that said Letters Patent is hereby corrected as shown below:

COLUMN 48

Line 38, "displayl" should read --display--.
Line 44, "compound," should read --compounds,--.

Signed and Sealed this

Eighth Day of March, 1994

BRUCE LEHMAN

Attest:

Attesting Officer

Commissioner of Patents and Trademarks